United States Patent [19]
Heilman et al.

[11] Patent Number: 5,078,134
[45] Date of Patent: * Jan. 7, 1992

[54] PORTABLE DEVICE FOR SENSING CARDIAC FUNCTION AND AUTOMATICALLY DELIVERING ELECTRICAL THERAPY

[75] Inventors: Marlin S. Heilman, Sarver; Arlan J. Brandt, Gibsonia; Larry D. Bowling; Joseph F. Russial, both of Pittsburgh, all of Pa.

[73] Assignee: Lifecor, Inc., Pittsburgh, Pa.

[*] Notice: The portion of the term of this patent subsequent to May 29, 2007 has been disclaimed.

[21] Appl. No.: 528,883

[22] Filed: May 29, 1990

Related U.S. Application Data

[63] Continuation-in-part of Ser. No. 185,781, Apr. 25, 1988, Pat. No. 4,928,690.

[51] Int. Cl.⁵ .............................................. A61N 1/00
[52] U.S. Cl. ................................ 128/421; 128/419 D; 128/783; 128/734; 128/696
[58] Field of Search ............ 128/421, 419 D, 419 PG, 128/696, 702, 734, 783

[56] References Cited

U.S. PATENT DOCUMENTS

| | | | |
|---|---|---|---|
| 3,241,556 | 3/1966 | Zacouto | 128/421 |
| 3,460,542 | 8/1969 | Gemmer | 128/421 |
| 3,702,613 | 11/1972 | Panico et al. | 128/417 |
| 3,826,245 | 7/1974 | Funfstuck | 128/2.06 |
| 3,942,533 | 3/1976 | Cannon, III | 128/417 |
| 3,961,623 | 6/1976 | Milani et al. | 128/2.06 |
| 4,002,239 | 1/1977 | Buchalter | 206/484 |
| 4,058,127 | 11/1977 | Buchalter | 128/417 |
| 4,088,138 | 5/1978 | Diack et al. | 128/419 |
| 4,576,170 | 3/1986 | Bradley et al. | 128/419 |
| 4,779,630 | 10/1988 | Scharnberg et al. | 128/783 |
| 4,785,812 | 11/1988 | Pihl et al. | 128/734 |
| 4,928,690 | 5/1990 | Heilman et al. | 128/421 |
| 4,974,600 | 12/1990 | Reyes | 128/419 D |

Primary Examiner—Francis Jaworski
Assistant Examiner—George Manuel
Attorney, Agent, or Firm—Fleit, Jacobson, Cohn, Price, Holman & Stern

[57] ABSTRACT

A patient-worn harness or vest protects at-risk patients from the possibly fatal results of heart arrhythmias. The harness or vest incorporates sensing electrodes for monitoring heart condition, a microprocessor and memory for processing signals received from the sending electrodes and comparing same with patient's data, and skin-contacting pulsing electrodes for applying electrical pulses to the patient's chest wall responsive to signals received from the microprocessor. The electrodes include automatic tightening and electrolyte gel release mechanisms for reducing impedance at the electrode-skin interface. A servicing subsystem is provided for the harness or vest and may be used to interface with the harness or vest and may be used to interface with the harness or vest and also to communicate with remote health care personnel through a suitable telephone link.

52 Claims, 28 Drawing Sheets

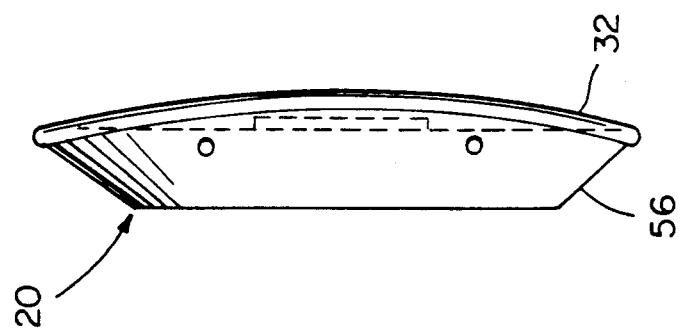
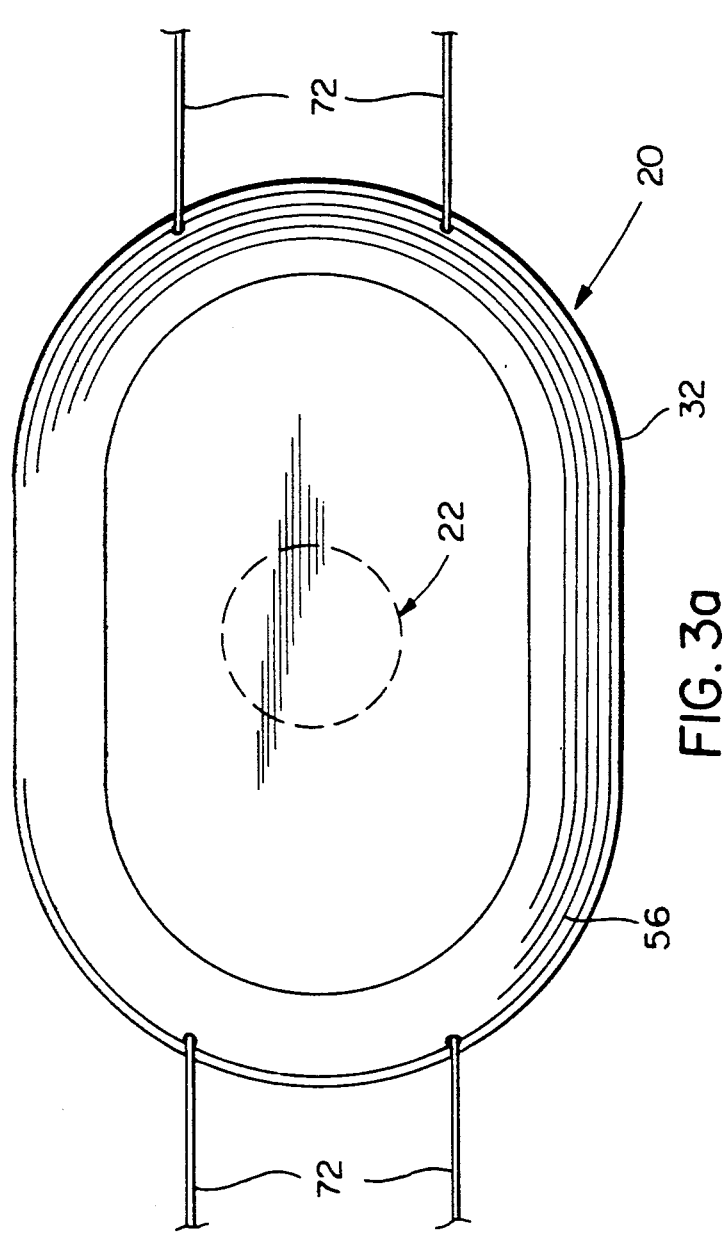
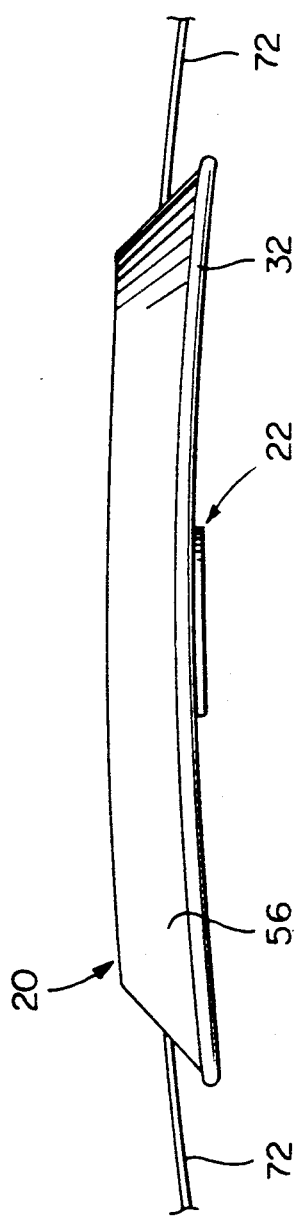

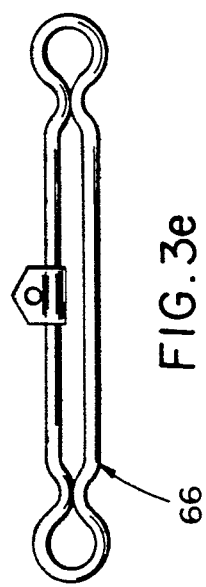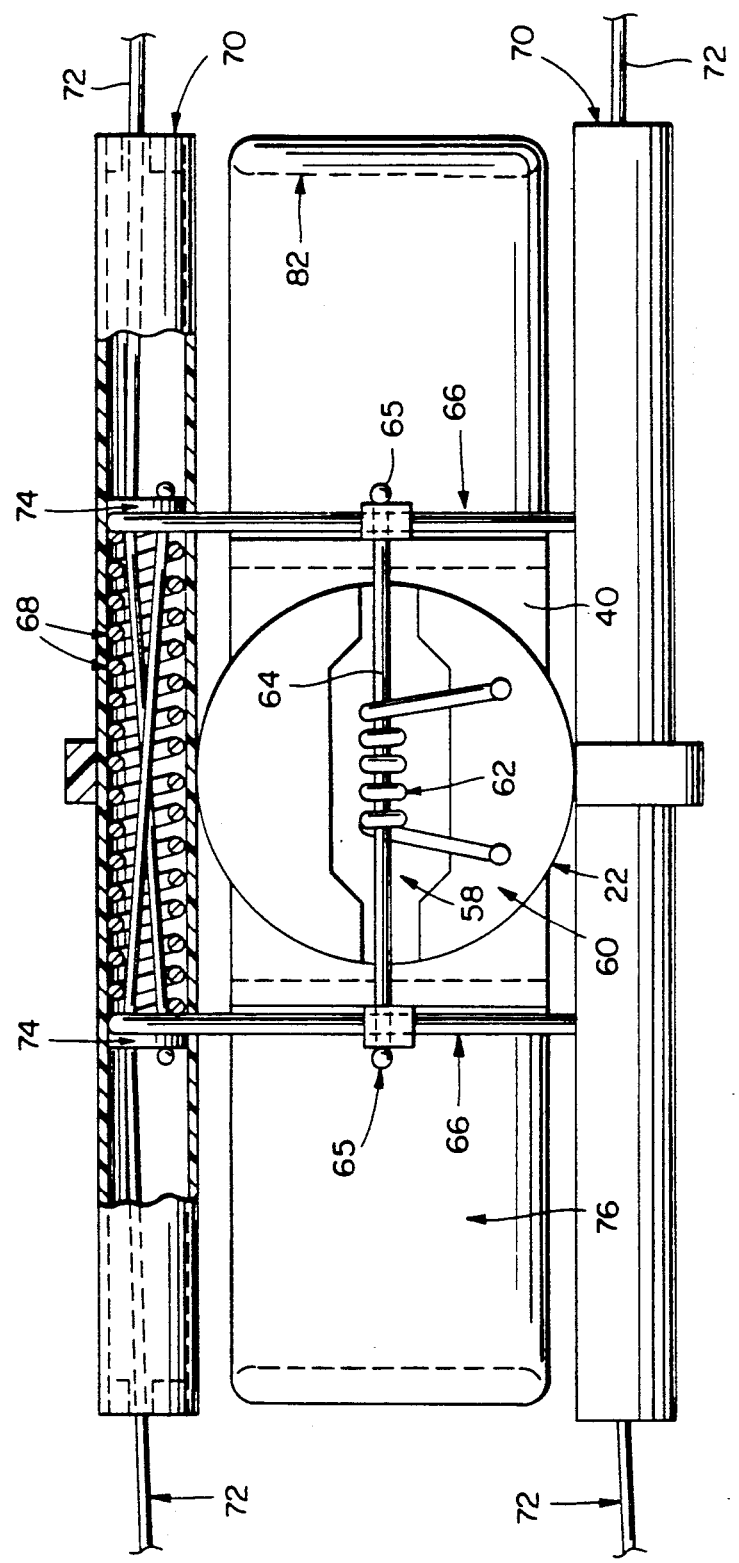

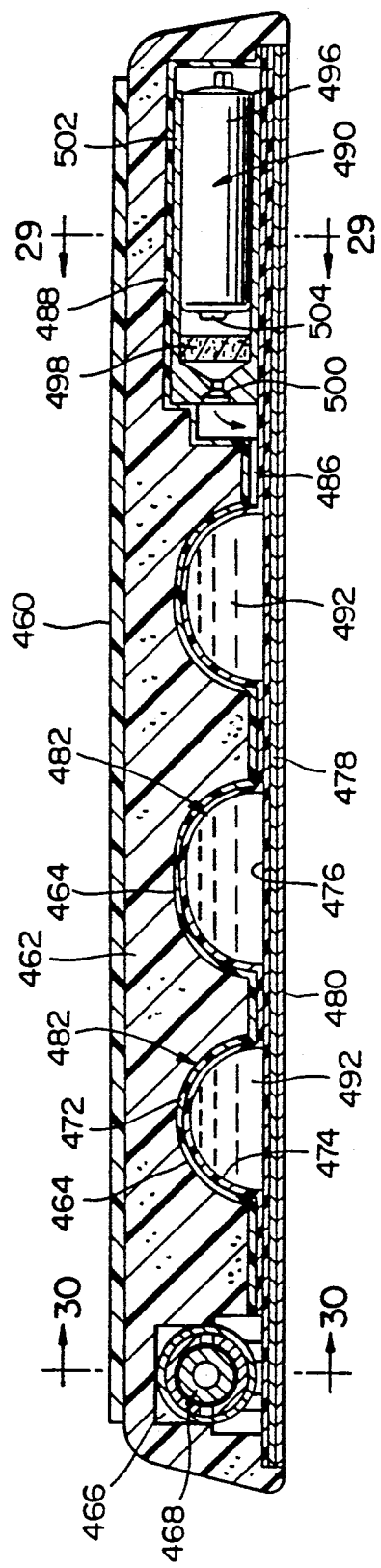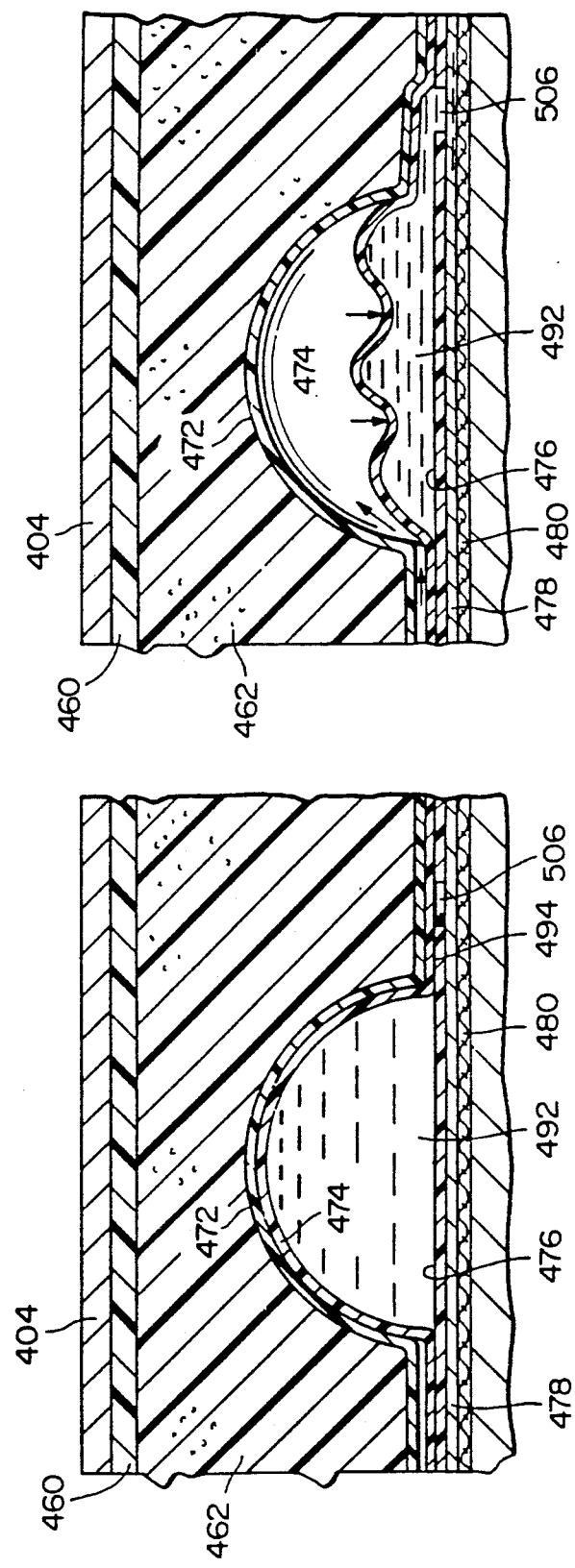

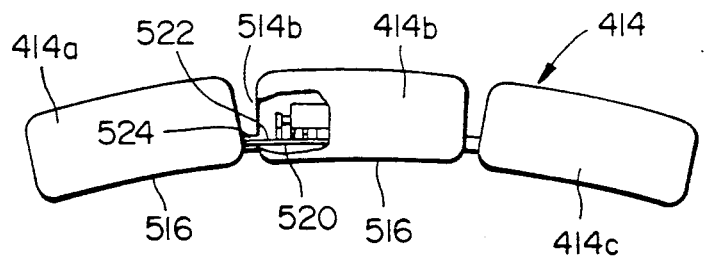
FIG. 33a
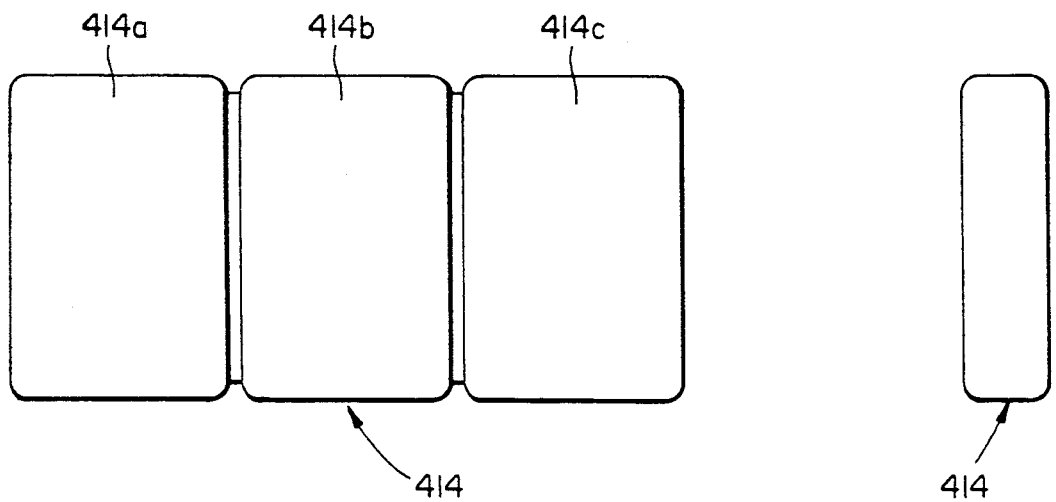
FIG. 33b
FIG. 33c
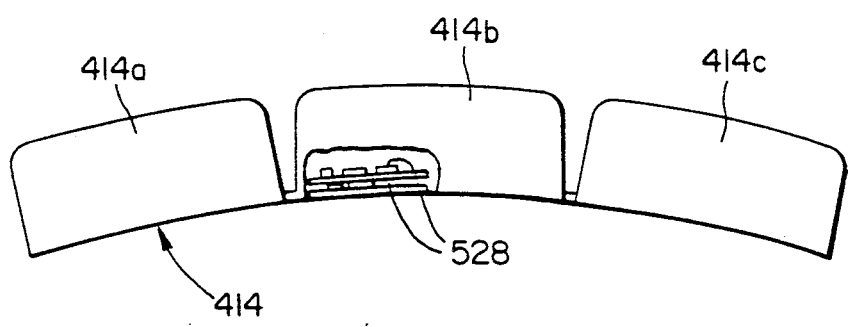
FIG. 34a
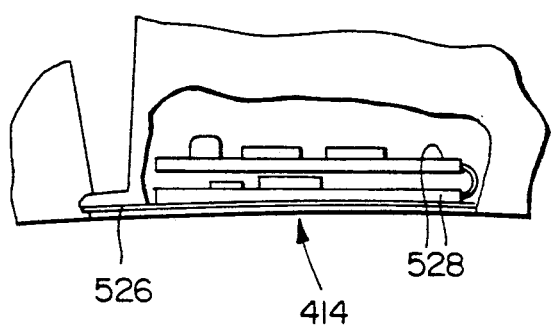
FIG. 34b

PORTABLE DEVICE FOR SENSING CARDIAC FUNCTION AND AUTOMATICALLY DELIVERING ELECTRICAL THERAPY

CROSS REFERENCE TO RELATED APPLICATION

This application is a Continuation in Part of application Ser. No. 07/185,781 filed Apr. 25, 1988, now U.S. Pat. No. 4,928,690 issued May 29, 1990, the entire contents of which is expressly incorporated herein by reference.

FIELD OF THE INVENTION

This invention relates generally to the treatment of human defects, particularly heart defects, by the administration of electrical therapy. More particularly, the invention relates to a system and means for protecting susceptible or at-risk patients from sudden death due to excessively fast or slow heart rates.

BACKGROUND OF THE INVENTION

For several years, technology has been available for correcting excessively slow heart rates (bradycardia) by implantable devices, commonly referred to as pacemakers, which deliver microjoule electrical pulses to a slowly beating heart in order to speed the heart rate up to an acceptable level. Also, it is well known to deliver high energy shocks (180 to 360 joules) via external paddles applied to the chest wall in order to correct excessively fast heart rates and prevent the possible fatal outcome of ventricular fibrillation or certain ventricular tachycardias. Bradycardia, ventricular fibrillation and ventricular tachycardia are all electrical malfunctions (arrhythmias) of the heart and each may lead to death within minutes unless corrected by the appropriate electrical stimulation.

Because time delays in applying the corrective electrical treatment may result in death, implantable pacemakers and defibrillators have significantly improved the ability to treat these otherwise life threatening conditions. Being implanted within the patient, the device continuously monitors the patient's heart for treatable arrhythmias and when such is detected, the device applies corrective electrical pulses directly to the heart.

Pacemakers and defibrillators that apply corrective electrical pulses externally to the patient's chest wall also are used to correct such life-threatening arrhythmias but suffer from a drawback insofar as it may not be possible to apply the device in time during an acute arrhythmic emergency to save the patient's life. Such treatment is needed within a few minutes to be effective. Consequently, when a patient is deemed at high risk of death from such arrhythmias, the electrical devices are implanted so as to be readily available when treatment is needed. Alternatively, such patients are kept in a hospital where corrective electrical therapy is generally close at hand. Long term hospitalization, however, is frequently impractical due to its high cost or due to the requirements for patients to engage in normal daily activities.

There are also many patients susceptible to heart arrhythmias who are at temporary risk of sudden death. For example, patients undergoing a coronary artery occlusion and myocardial infarction are at substantial risk of tachyrhythmia for several weeks following the coronary artery occlusion. Such patients are generally hospitalized but could be discharged earlier if there was a practical means to protect them from life threatening arrhythmias. There are also numerous patients awaiting implantation of an automatic defibrillator who require an external defibrillator to be close at hand in case they experience a life-threatening tachyrhythmia. Additionally, there are patients in need of an implantable defibrillator who are placed at inordinate risk due to the surgery required for implanting such a device.

It is evident from the above that there is a real need for providing an effective means whereby susceptible patients can be protected on a relatively long-term basis against the dangerous consequences of an electrical heart malfunction without having to undergo an implant procedure and without having to remain hospitalized.

SUMMARY OF THE INVENTION

It is an object of the invention to provide a system and means as referred to above, whereby a patient susceptible to certain heart arrhythmias can be effectively protected against harmful consequences resulting therefrom without having to undergo an implant procedure and without having to remain hospitalized.

Another object of the invention is to provide an effective form of externally applied electrical therapy which can provide relatively long-term protection to a patient against the consequences of heart arrhythmias without the patient having to forego normal everyday activities.

A further object is to provide treatment apparatus which can be comfortably worn by a patient on a relatively long term basis and which is adapted both to detect a treatable condition in the patient and, in response thereto, provide electrical therapy to the patient.

The present invention provides a system and means whereby susceptible patients may be substantially protected from arrhythmic death including a portable patient-worn external pacemaker/defibrillator that is comfortable to wear yet has the capability of continuously monitoring the patient for potentially lethal arrhythmias and delivering corrective electrical pulses quickly and appropriately in the event that such arrhythmia occurs. The invention also provides a supportive non-patient-worn system and means to optimize the operational readiness and reliability of the patient-worn device. Emphasis in the present inventive system and means is placed on optimizing reliable operation and further on maximizing patient compliance in wearing such a device by making the device comfortable and user compatible.

Further, according to the present invention, there are provided a number of means whereby the automatic external pacemaker/defibrillator may be worn comfortably by an at-risk patient. Included are means to minimize the weight of the device, means to distribute the weight-bearing surfaces over a large body area, means to allow the device to be loosely fitting in a standby mode, and means to allow a comfortable undergarment to be generally positioned between the device and the patient's skin. Most importantly, the device also includes means to cause a low impedance pathway to be established for an electrical pulse to the heart when a potentially dangerous arrhythmia has been detected by the device.

Correct reliable positive detection of arrhythmias and minimal false detections are important to the utility of the wearable anti-arrhythmic device. Accordingly, it is also preferred that the device continuously monitor more than one physiological indicator of a treatable arrhythmia. Since various types of patient behavior may produce unreliable detection, means may be provided for advising the patient of the status of the detection circuits such that the patient may learn behavior patterns that optimize reliable device operation. The device may also include means whereby the patient may delay the delivery of a high energy shock if conscious, indicating that the arrhythmia is not yet life-threatening.

It is a further object of the invention to provide different types of system monitoring means to maximize safety, efficacy and reliability of the patient-worn device. Such monitoring means may include means to check operational readiness of the patient-worn device, means to check battery status of the device, means to recharge the batteries if necessary, means to record memory contents of the patient-worn device, and means to transmit vital data to remote health care personnel for problem solving and advising on correct device operation.

The above and other objects that will hereinafter appear, and the nature of the invention, will be more clearly understood by reference to the following description, the appended claims and the accompanying drawings.

BRIEF DESCRIPTION OF THE DRAWINGS

FIG. 3a is a plan view of a first embodiment sensing and pulsing electrode assembly used in the defibrillator device;

FIG. 3b is a side elevational view of the electrode assembly;

FIG. 3c is an end elevational view of the electrode assembly;

FIG. 3d is an enlarged plan view, partly broken away, of the interior of the electrode assembly with the cover removed;

FIG. 3e is an end elevational view of one of the electrode components;

FIG. 26 is a sectional elevation view of the front treatment electrode on line 26—26 of FIG. 25;

FIG. 27 is an enlarged sectional view of a part of the front electrode prior to use;

FIG. 28 is a view similar to FIG. 27 during release of fluid from the electrode;

FIGS. 33a, 33b and 33c show a plan view (part broken away), a front view, and an end view of one embodiment of a segmented chest-worn treatment package;

FIGS. 34a and 34b show broken-away plan views of respective embodiments of the chest-worn package.

DETAILED DESCRIPTION OF THE PREFERRED EMBODIMENTS

Figure 4:
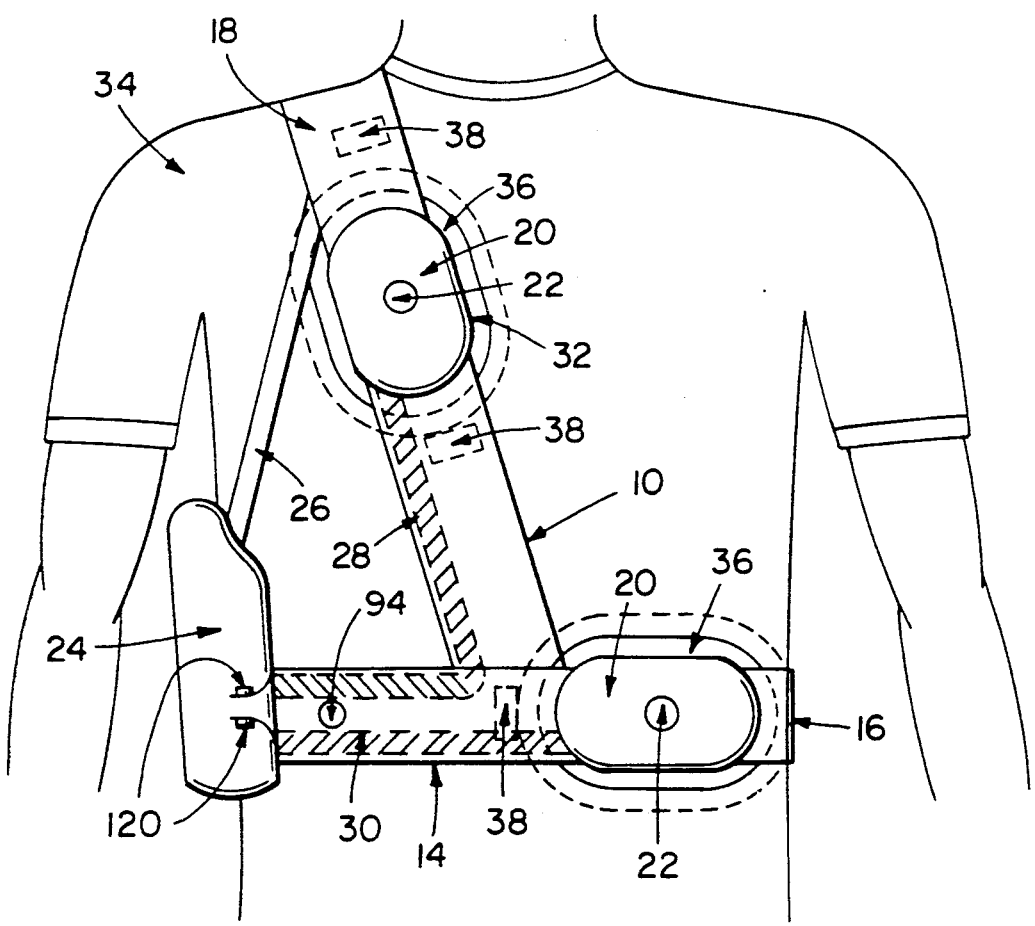
FIG. 4 is a diagrammatic in-use view of the first embodiment pacemaker/defibrillator as worn by a patient.
Figure 6:
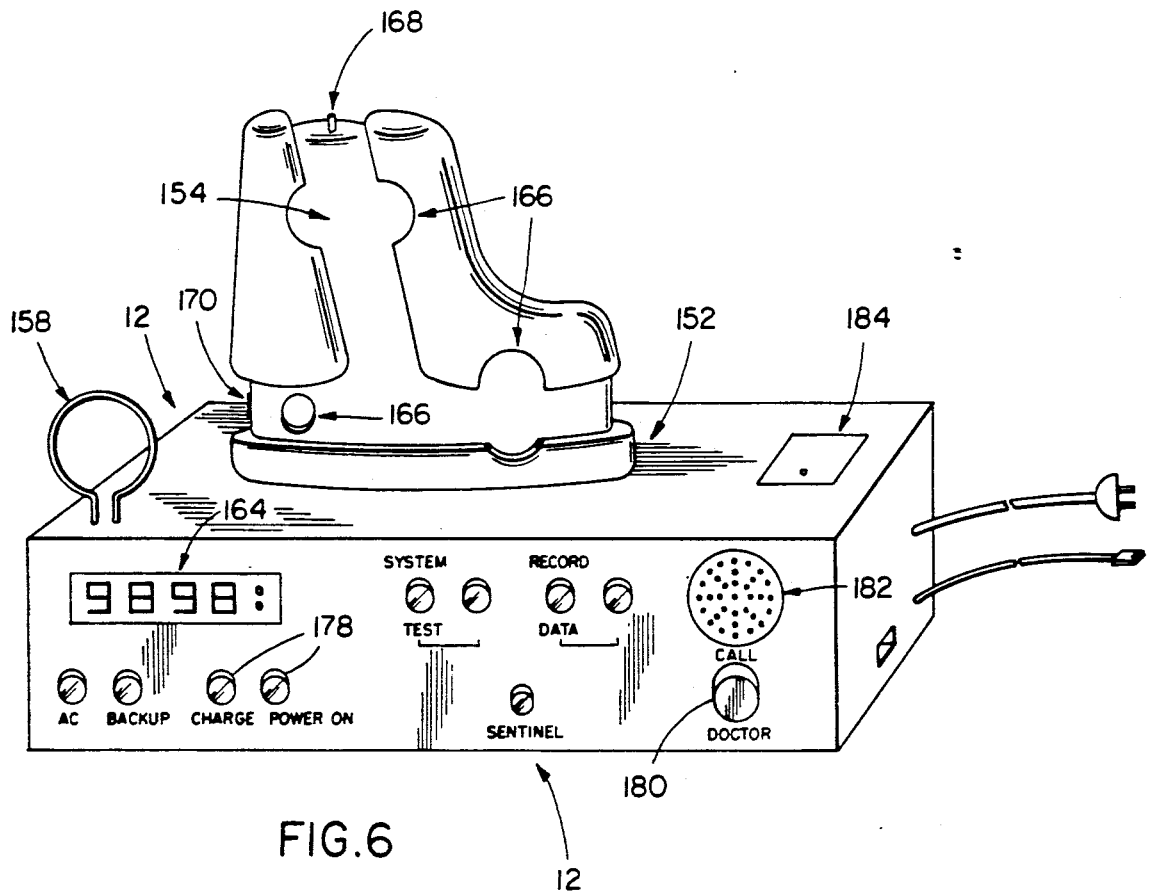
FIG. 6 is a diagrammatic perspective view of the maintenance subsystem.
Figure 7:
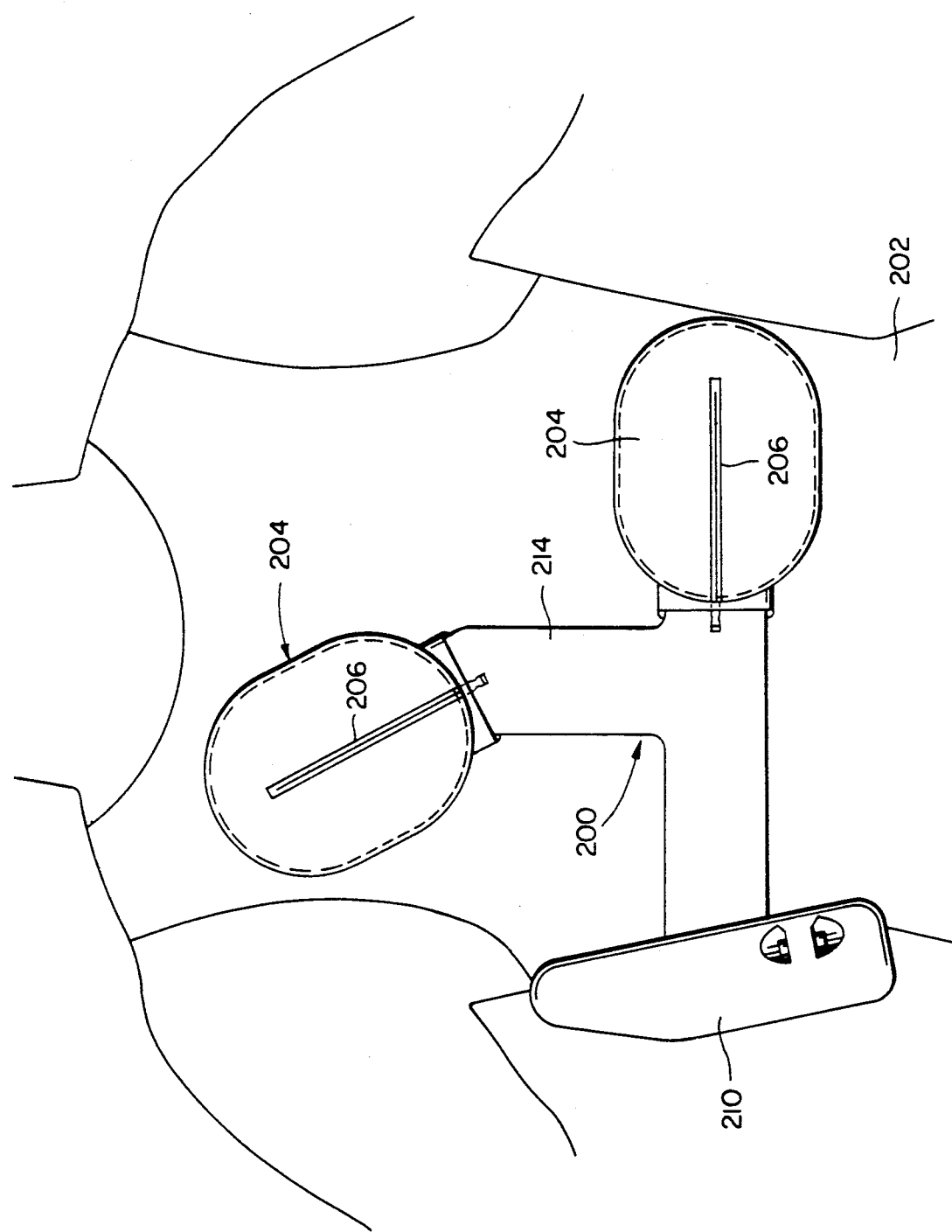
FIG. 7 is a diagrammatic in-use view of a second embodiment pacemaker/defibrillator device in accordance with the invention, shown in association with an upper-body garment with which it is worn.
Figure 8:
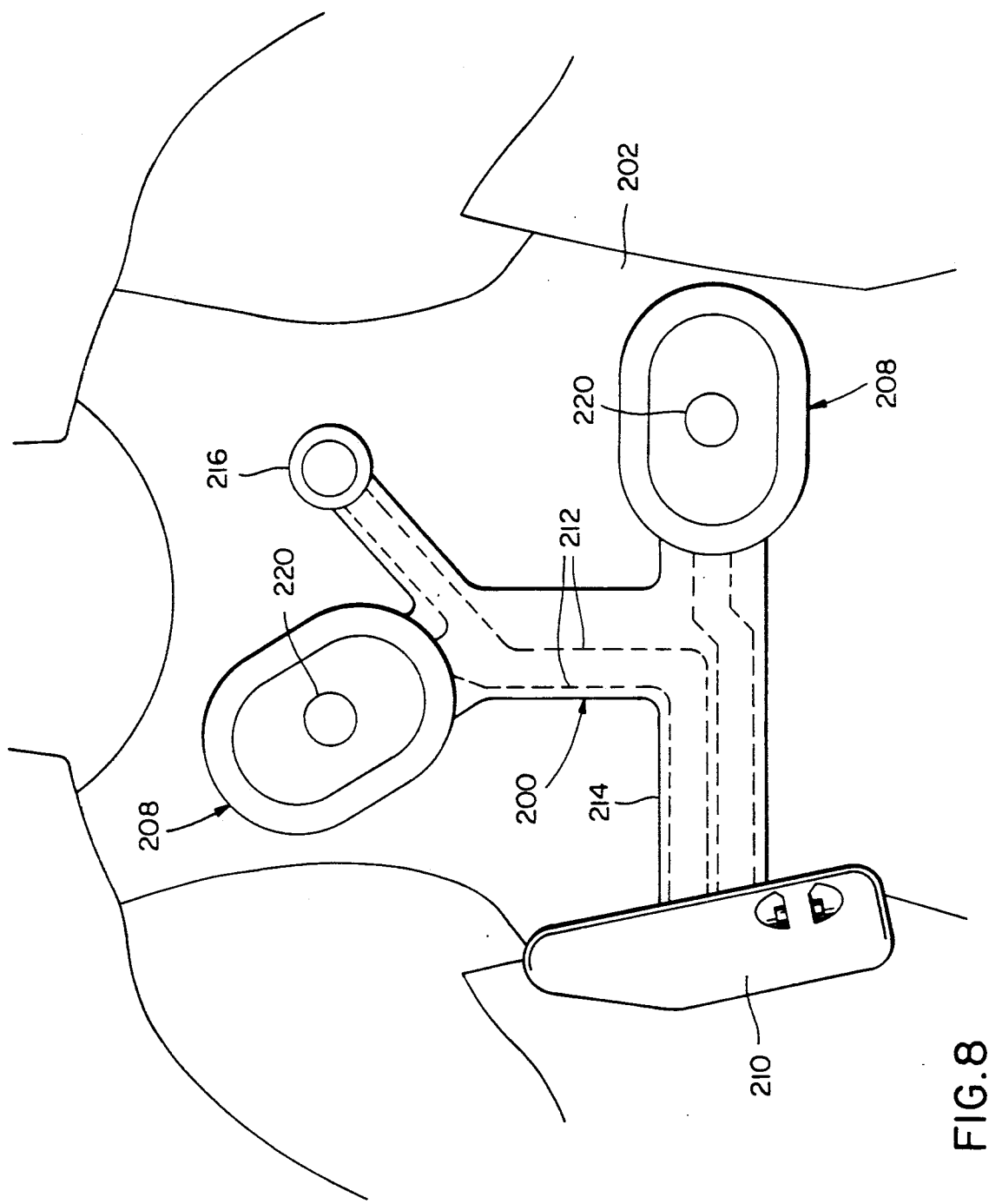
FIG. 8 is a view of the second embodiment pacemaker/defibrillator device in it in-use position, and shown in somewhat more detail.

Generally stated, in a preferred form of the invention as illustrated in the drawings, there is provided a patient-wearable automatic electric heart therapy device, such as device 10, shown in overall view in FIG. 4, or device 200 shown in overall view in FIGS. 7 and 8, and a maintenance subsystem or module 12, shown in overall view in FIG. 6 on which the respective therapy device 10 or 200 can be mounted when not in use on a patient, effectively to service, program and charge the device.

As shown in FIG. 4, in a first embodiment, the patient-worn device may include a waist-encompassing belt 14 of suitable fabric, webbing or the like, which may be elasticized, or may incorporate sprung elements the belt having a low-profile connector or buckle 16, and a shoulder strap 18 of like material connected between front and rear portions of the belt. First and second like sensing and pulse electrode assemblies 20 are carried respectively on belt 14 and shoulder strap 18. Belt 14 also carries a pulse generator 24 which may have a supporting strap connection 26 with strap 18 and electrical conductors, diagrammatically indicated at 28 and 30, for receiving electrical signals from and delivering electrical pulses to the respective electrode assemblies 20. Assemblies 20 have respective sensing electrodes 22 and pulse electrodes 32.

In use of the device as thus far described, assemblies 20 are held in comfortable contact with a patient's chest wall and continuously monitor and detect the heart rhythm by means of the respective sensing electrodes 22. Alternatively, sensing electrodes may be traditional disposable E.C.G. electrodes placed on the patient's skin in a location separate from the pulse electrodes 32. In the event that the sensing electrodes detect a treatable heart arrhythmia, the electrodes will send the sensed signal via conductors 28 and 30 to the pulse generator, and in response thereto, the pulse generator will return appropriate treatment pulses to the respective pulse electrodes 32. Moreover, each of the electrode assemblies further includes means (to be described below) for automatically reducing the impedance of electrical transmission to the heart upon receipt of the appropriate treatment commencing signal from the pulse generator. Such impedance reducing means may include, for example, means for automatically tightening the respective pulsing electrodes 32 against the patient's skin, and means for automatically releasing an electrically conductive electrode gel to the electrode-skin interface.

Reverting to FIG. 4, it is seen that device 10 may be worn over a comfortable undergarment 34, such as a T-shirt, which may have apertures 36 that receive the respective electrode assemblies 20. Attachments 38, such as patches of loop and pile Velcro-type fabric, may be provided between belt 14, strap 18 and the undergarment.

Figure 2A:
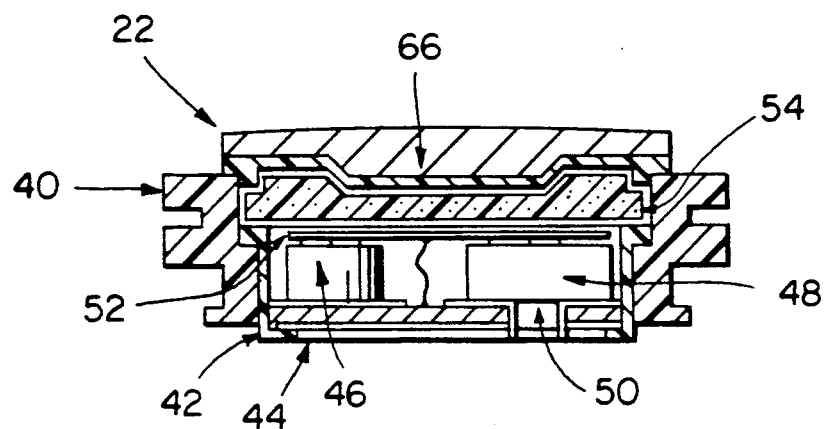
FIG. 2a is a diagrammatic sectional elevational view of a first embodiment combination ECG electrode/heart sound microphone used with the pacemaker/defibrillator device for heart beat detection.
Figure 2B:
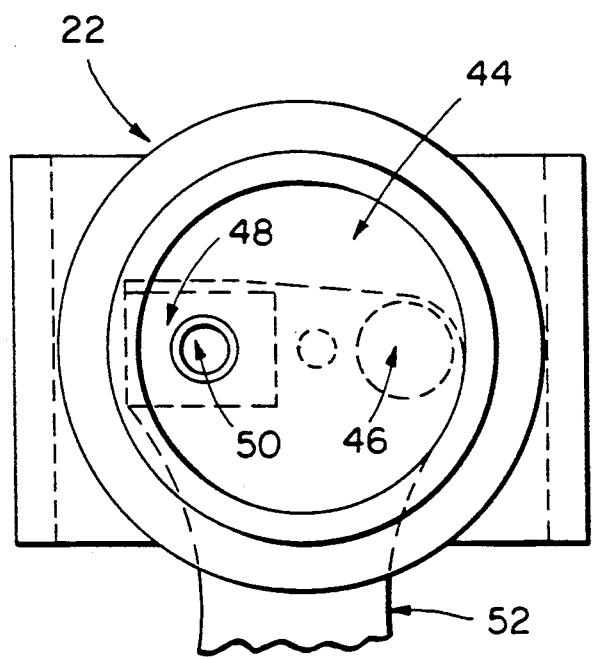
FIG. 2b is an underneath plan view of the microphone.

FIGS. 2a and 2b illustrate details of the respective sensing electrodes 22. Each sensing electrode, which is centrally located in its respective assembly 20, comprises a plastic, cylindrical housing 40 containing a telescoping inner chamber 42 which carries an EGG electrode 44, an associated amplifier 46, and an audio transducer or microphone 48. The EGG electrode 44 may be capacitive, conductive carbon, or any other design which permits long-term use without skin irritation. The microphone is acoustically coupled to a port 50 which conducts audio-frequency energy to the microphone diaphragm. The diameter of the inner chamber is typically about 2.5 cm. Installed over the amplifier 46 and microphone 48, and electrically connected thereto, is a flexible printed circuit 52 supplying power to and receiving signals from the amplifier and microphone. It is understood that the printed circuits of the respective electrodes are connected to the pulse generator 24 through conductors 28 and 30 referred to in connection with FIG. 4.

The inner chamber 42 telescopes within the outer chamber 40 and a synthetic expanded foam pad 54 located beneath a chamber cover 60 applies pressure to the top of the inner chamber and thus to the skin surface, insuring constant contact between the ECG electrode surface and the skin whenever the system is worn.

Figure 3F:
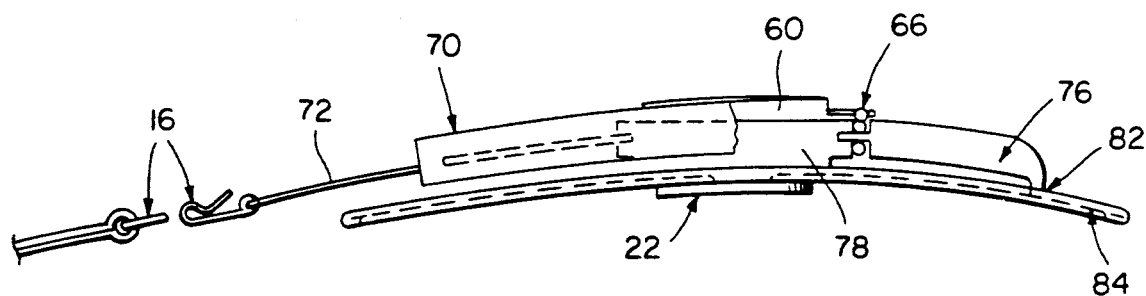
FIG. 3f is a side elevational view of the electrode assembly with the cover removed.

FIGS. 3a–3c illustrate the overall outer appearance and dimensions of the respective electrode assemblies 20, showing the placement of the sensing electrode 22 within the pulse electrode 32. The electrode assemblies each have an outer housing 56 of a flexible, composite material having a skin contact area of approximately 100 square centimeters.

FIGS. 3d–3g illustrate the interior of the respective electrode assemblies with the housing removed. The respective sensing electrode 22 fits centrally within the respective pulse electrode and has a recess 58 provided in the top surface of the central chamber cover 60. Recess 58 contains an electrically-operated release or trigger mechanism, consisting of a heating coil of resistance wire 62 wound around a synthetic fiber activator member 64. Member 64 has headed ends 65 which attach to and retain two spring-loaded equalizer bars and allowing springs 68 to exert force upon the bars which travel within two cantilevered tubes 70. Contained within tube 70 are synthetic fiber tension members 72, fastened at their ends to washers 74 and at their other ends, not shown, into the structure of belt 14 or strap 18 as the case may be. Thus, as the equalizer bars travel within the tubes, the tension members 72, by virtue of their attachment to the washers, are pulled through the tubes, applying tension to the ends of the belt 14 or strap 18 to which the respective electrode housing fastens, thereby tightening the electrode assembly against the patient's skin and providing a firm form of impedance reducing means.

Figure 3G:
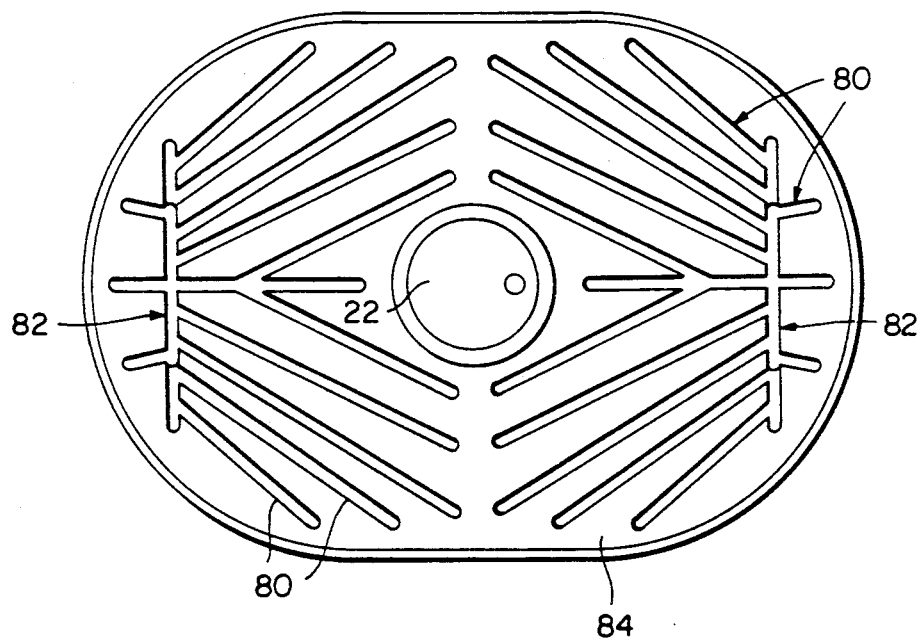
FIG. 3g is an underneath plan view of the electrode assembly with the cover partly removed.
Figure 3H:
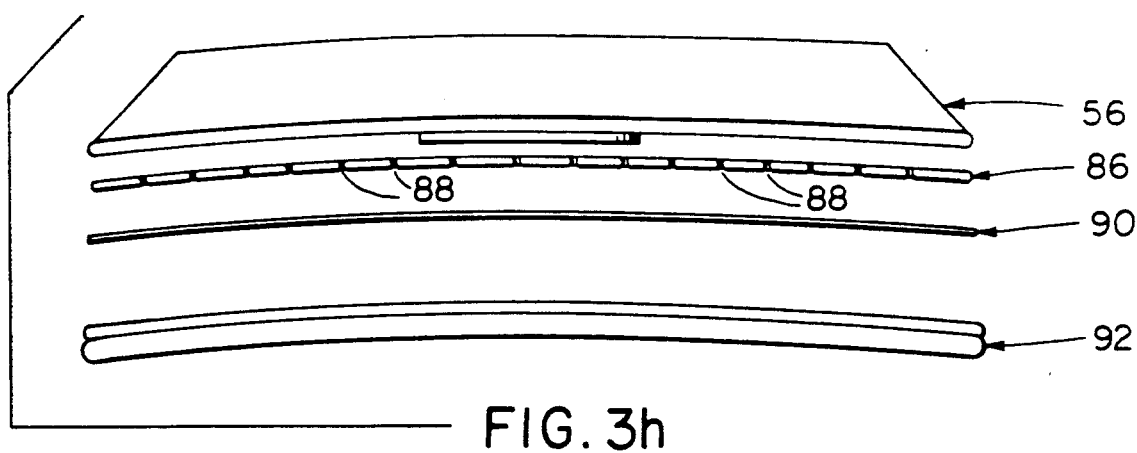
FIG. 3h is an exploded elevational view of parts of the electrode assembly.

Between the tubes 70 at each side of the electrode body, and attached to grooves in central housing 40, are opposite capsules 76 containing a conductive fluid such as an electrolyte gel. Central portions of the equalizer bars 66 surround the gel capsules such that when activated, the bars move along and compress the capsules and extrude the gel toward the ends of the electrode assembly away from central housing 40. Elongated ports 82 at the outer ends of the capsules 76 communicate with channels 80 in a base member 84 of the electrode body. FIG. 3g is a bottom view of the electrode assembly illustrating the gel channels 80 radiating from the capsule ports 82, and FIG. 3h is an illustration of the cross section of the skin-contacting surface. The gel channels are open along their length but base member 84 is covered by a restrictor plate 86 with restricted openings 88 which communicate with the respective channels.

The dimension of the gel channels are such that there is little impedance to the flow of conductive gel over the length of the channels, but the openings 88 impede the gel flow somewhat. This differential flow resistance ensures that upon activation of the extruder mechanism, the conductive gel rapidly fills all of the channels and then slowly the gel will be extruded through the holes in the restrictor plate. After passing through the plate, the gel then infiltrates a metallic mesh or perforated foil pulse electrode plate 90, which carries the current necessary for the electrical treatment, whether it be pacing, cardioverting or defibrillating. As the gel wets the metallic member, the electrical connection to the skin is enhanced by significantly lowering the impedance at the interface and providing a second form of impedance reducing means.

In the dry, non-activated state, a comfortably soft and absorbent fabric 92 covers plate 90 and contacts the patient's skin. This fabric typically is cotton. The fabric may be sewn through the surface of the electrode or may be loosely fitted onto the electrode with edges that curl over the electrode's edge and are held taut by an elastic member. This latter configuration allows frequent exchanges of the fabric surface for cleanliness purposes.

Figure 5A:
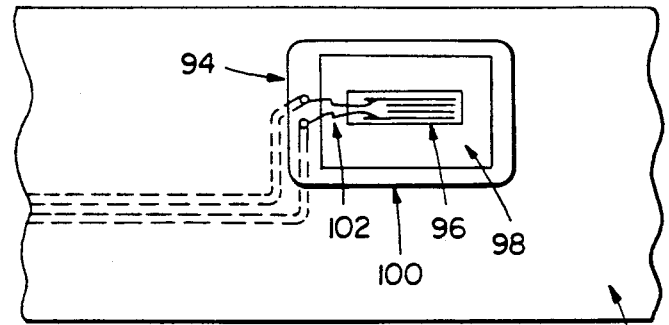
FIG. 5a is a diagrammatic plan view of a respiration sensor as used in the first embodiment pacemaker/defibrillator device.
Figure 5B:
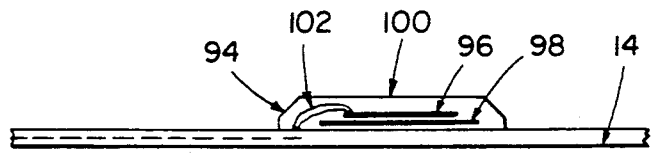
FIG. 5b is a diagrammatic elevational view of the respiration sensor.

FIGS. 5a and 5b illustrate a belt mechanism 94 which may be used to sense respiration movement. A strain gauge 96 is bonded to a metallic backing plate 98 which is attached firmly to belt 14. A protective molded cover 100 is applied over the gauge element which also encapsulates lead wires 102.

System operation will now be described with particular reference to FIG. 1.

A set of sensors (monitoring means) is used to gather information as to the patient's condition. The monitoring means include the respiration sensor 94, previously described, for detecting chest wall movement, the microphone 48 for picking up heart or respiration sounds, the ECG electrodes 22 to monitor the surface electrocardiogram and a reference ECG electrode 106 (known per se) to establish a "common" potential for electrodes 22. The signals from the sensors are amplified and conditioned by respective amplifiers 108, 110, 112 and a signal processing network 114. The conditioned signals are applied to a microprocessor 116.

The microprocessor, in conjunction with a system memory 118, performs all functions necessary for patient monitoring, time keeping and background operation, recording of arrhythmias and system events, communication with the maintenance subsystem 12, control of treatment sequences, self checks of system and electrode functioning, and monitoring of status switches 120 and 122. The microprocessor and memory together constitute essential elements of the pulse generator 24 described in connection with FIG. 4. These items are well known per se in heart treatment equipment and will not be described in further detail.

Also contained in the system memory 118, are tests and conditions for declaring a treatable event. When a treatable event is sensed, the microprocessor will initiate treatment as programmed in the system memory. Treatment modes and sequences may be individually personalized for each patient and may include low or high energy cardioversion/defibrillation, and a wide range of pacing modalities.

When a treatable event is sensed, the microprocessor activates the pressure means 124 (namely, the release mechanism 62 previously described) which pulls the pulsing electrodes 32 tightly against the patient's chest wall. Simultaneously, the electrode gel 126 is released by the treatment electrode as previously described to produce a low resistance contact. An impedance sensing circuit 128 is incorporated in the system to verify that the low resistance condition exists. At this point, the microprocessor may issue a spoken warning to stand clear via a voice synthesizer 130 and speakers 132, and causes treatment to begin through the pulsing electrodes, either pacing by a pacing circuit 134 or high energy shock by a defibrillator circuit 136. The patient, at his or her option, may delay treatment by simultaneously depressing two "live man" switches 120. If the patient subsequently looses consciousness and releases the switches, treatment will begin; otherwise, the treatment is delayed.

Other functions which may be included in the system are an RF communications link to the maintenance system via receiver/transmitter 140 and antenna 142, and a power supply 144 which may have a rechargeable battery pack 146 to be charged by plugging into a charging port 148 on the maintenance system. An "on patient" sensor (switch 122) may be provided to inform the microprocessor that the device is in place on a patient. A self test feature may also be incorporated. Thus, by depressing one of the "live man" switches, the patient may initiate a test program which will report device status and/or any fault condition via speaker 132.

Figure 1:
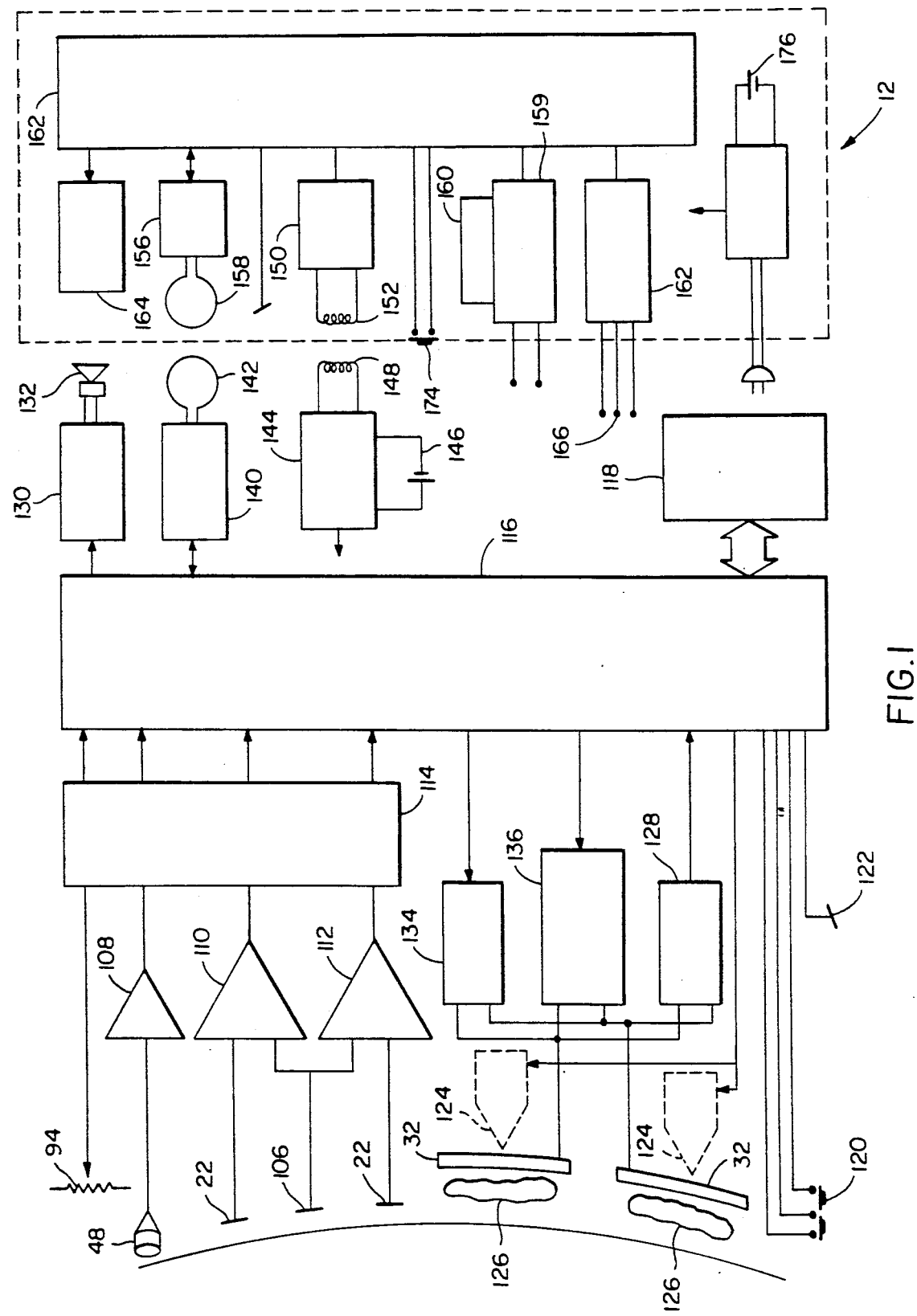
FIG. 1 is a block diagram of the functional elements of a first embodiment wearable automatic pacemaker/defibrillator device and maintenance subsystem for the wearable device.

The maintenance subsystem 12, a block diagram of which is shown on the right hand side of FIG. 1, may comprise a microprocessor-based support device for the belt device 10. The main functions of the maintenance subsystem are to provide a charger 150 for the belt power supply 144 and a communications link, for example between the belt and a telephone line. The charging may be effected either when the belt is on the maintenance device 12 using a built-in charging coil 152, or this coil may be extensible for remote use while the patient is wearing the belt. Alternatively, charging may be effected by alternating two battery packs. Communication with the belt is through an RF link 156 and an antenna 158. Communication with a telephone line is through a telephone dialer and modem 159 and a built-in speaker phone 160.

Other possible functions of the maintenance system will also be described. Thus, in FIG. 1, reference 162 is a microprocessor and system memory. The microprocessor controls all system functions. It also serves as the system clock with a time and status display 164. The system memory preferably is large compared with the belt memory, allowing it to store more of the patient's electrocardiogram and other data. The belt memory may be periodically "dumped" into the maintenance system for storage and eventual relay to a physician via telephone.

The maintenance system may also serve as a test system for the belt. For this purpose, test electrode outputs 166 (FIG. 6) may be located, such that when the belt is on the maintenance system, as determined by a sensor 168, the ECG test electrodes are in proximity to the belt pickup electrodes. Similarly, a respirator transducer 170 and a microphone test transducer 154 may be located near their corresponding sensors. This allows a full functional check of the belt sensing and detection mechanisms using test circuitry 162 (FIG. 1). This testing can be done automatically or initiated by the patient using a test button 174.

The maintenance system may be powered by an AC line and may incorporate a back-up battery 176 in case of a power outage. Other features may include power and charging status lights 178, a single button 180 for emergency dialing of a physician, or other off-site sources of medical assistance, allowing diagnosis and treatment by telephone during an emergency, and a built-in speaker phone 182 for convenience. A compartment 184 may be provided for charging coil storage.

The monitoring means may be adapted for detecting QRS electrical depolarization of the patient's heart and the patient's rate may be determined from the interval between QRS detections. Additionally, the rate of change of the patient's heart rate may be monitored. Also, or alternatively, the presence of an aortic valve closure sound may be used to verify or substitute for the sensing of a QRS electrical complex. A treatable tachycardia may be declared when the patient's heart rate exceeds a preset value for a preset time duration and the heart rate of change exceeds a preset level. A treatable bradycardia may be declared when the patient's heart rate drops below a preset rate for a preset time duration. Further, gasping motion or respiration may be used as a detection parameter for delivering a high-energy defibrillating shocks and may be used in combination with fast heart rate and/or fast heart rate acceleration for indicating the need for delivering of a high energy defibrillating shock.

As shown in FIGS. 7 and 8, a second embodiment heart therapy device 200, of similar functioning to the first embodiment device 10, may be worn with a comfortable, vest-like upper body garment structure 202, which may be form fitting and elasticized to ensure adequate contact of the sensing transducers with the skin surface, as will be described. The vest is constructed with sewn-in pockets 204 equipped with slide fasteners 206 or other positive-acting closures, into which electrode assemblies 208 of the device 200 are inserted prior to patient use, with pulse generator 210 of the device suitably attached to the vest and a conductor system 212 extending between the respective electrode assemblies and the pulse generator. It is understood that device 200 may be in the form of a self-contained treatment package with the conductors being contained in a suitable sheath 214 or the like which connects the various subassemblies. The device may also include a respiration sensor 216. The arrangement permits multiple vests to be on hand for cleanliness purposes, and allows the treatment package to be rapidly and easily changed between vests, ensuring relatively uninterrupted sensing and treatment.

The vest may additionally be fitted with appropriately located reinforcement sections, which upon receipt of a treatment-commencing signal from the pulse generator, translates movement of an upper half of the respective electrode housing into radial pressure against the patient's skin. As in the previous embodiment, the vest may have apertures allowing the respective electrode assemblies to contact the patient's skin. Additionally, the vest may have attachment means along its lower edge for attaching same to a belt, a lower body garment, or the like.

Figure 9A:
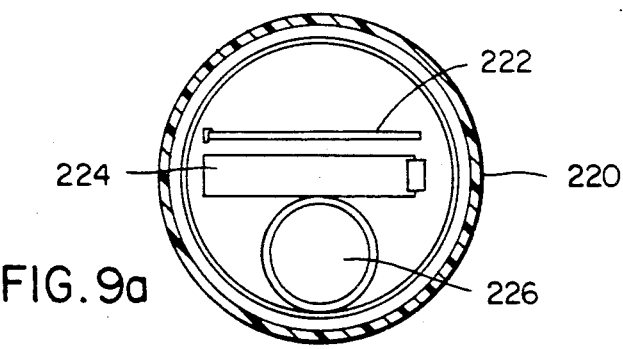
FIGS. 9a and 9b are sectional plan and sectional elevational views respectively of a sensing electrode assembly used in the second embodiment device.
Figure 9B:
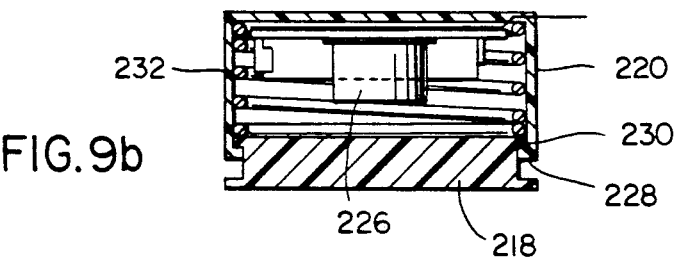

Each of the two ECG sensing/pulse delivery electrode assemblies 208 includes an ECG sensing electrode 218 (FIG. 9b) located within a plastic cylindrical housing 220, which is centrally located within the respective assembly 208. Electrode housing 220 contains the flexible, conductor-fiber-filled sensing electrode 218, two motion-detecting elements 222, 224, and associated amplifiers 226. The sensing electrode 218 is free to move vertically within the housing, but is limited in travel by molded-in bosses 228, 230. A spring 232 located beneath the chamber cover applies pressure to the top of the sensing electrode and thus to the patient's skin surface, ensuring constant contact between the ECG electrode surface and the skin whenever the system is worn.

Figure 10A:
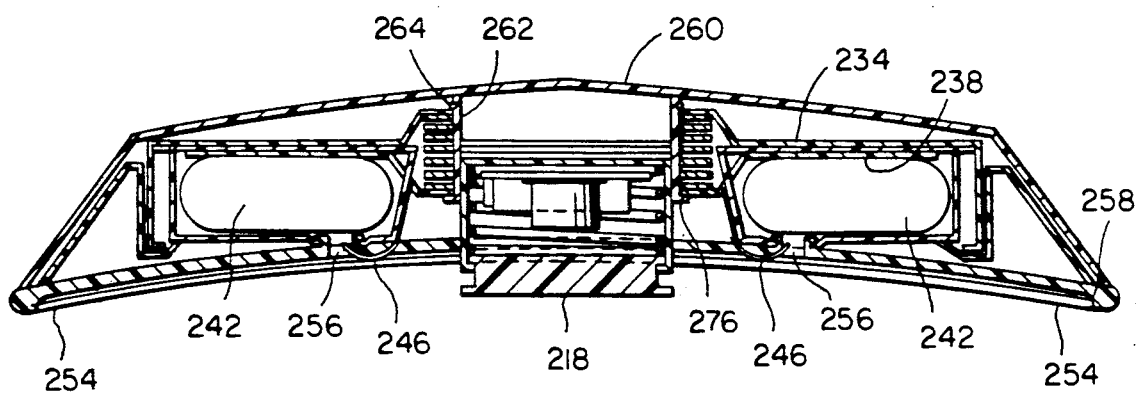
FIGS. 10a and 10b are sectional elevational views of a pulsing electrode assembly used in the second embodiment device, FIG. 10a showing the assembly in a holding mode, and FIG. 10a showing the assembly in an operational mode.
Figure 10B:
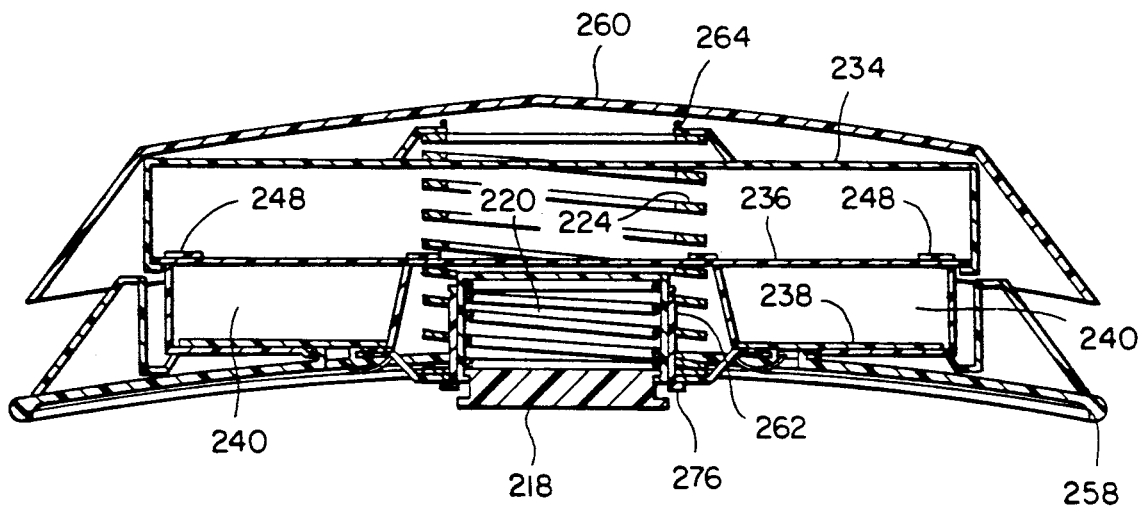
Figure 10C:
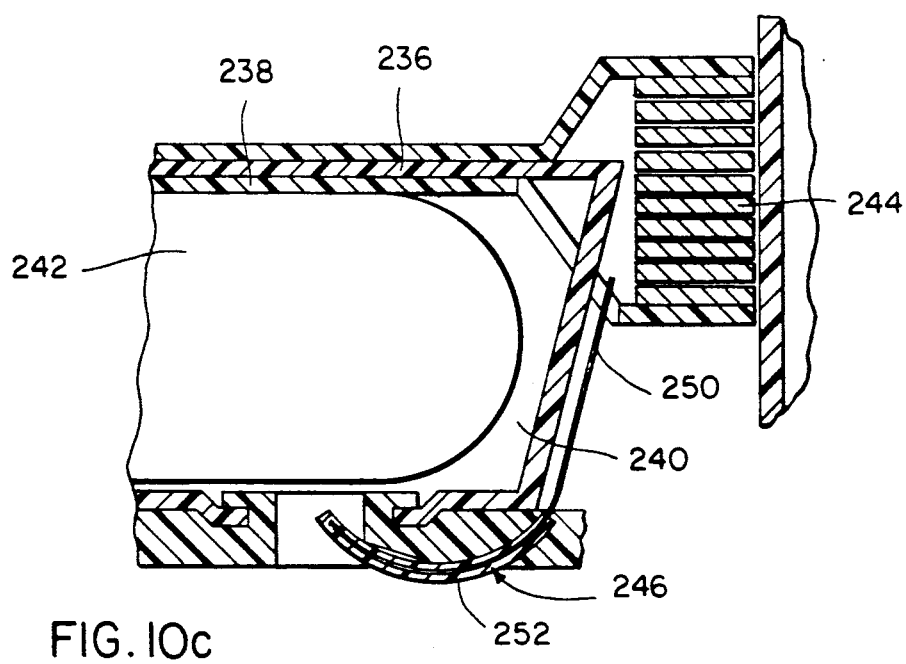
FIGS. 10c, 10d and 10e are enlarged sectional elevational views of parts of the pulsing electrode assembly when in the holding mode.
Figure 10D:
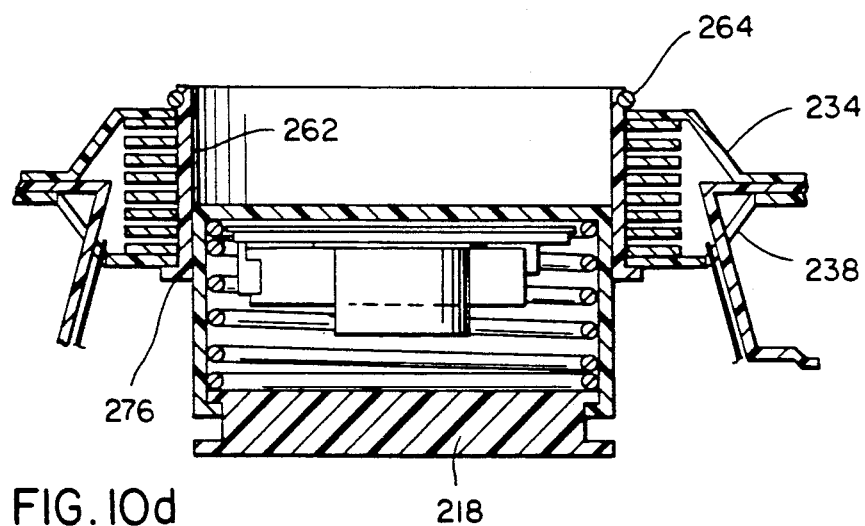
Figure 10E:
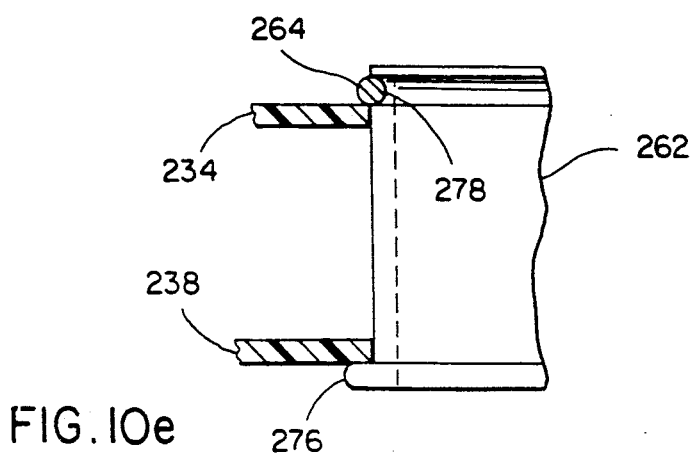
Figure 11A:
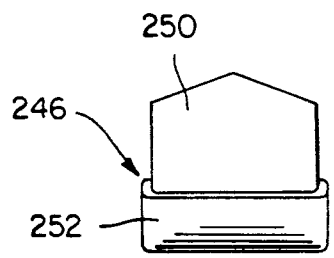
FIGS. 11a, 11b and 11c show respective parts of the puncture mechanism in the operational mode.
Figure 11B:
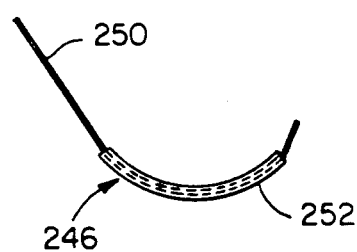
Figure 11C:
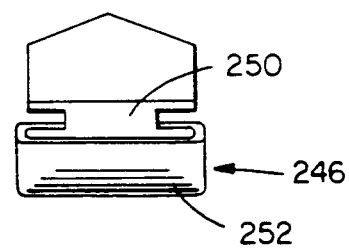
Figure 11D:
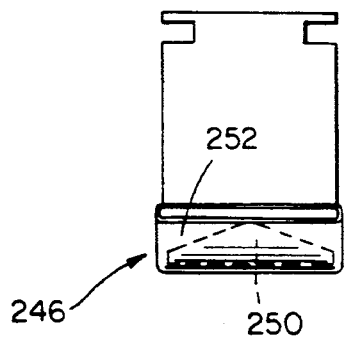
FIGS. 11d, 11e and 11f show the respective parts in the holding mode.
Figure 11E:
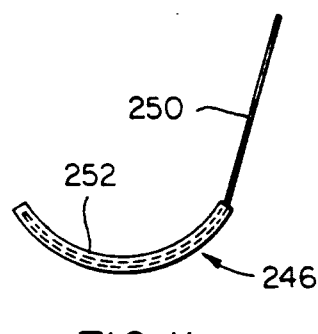
Figure 11F:
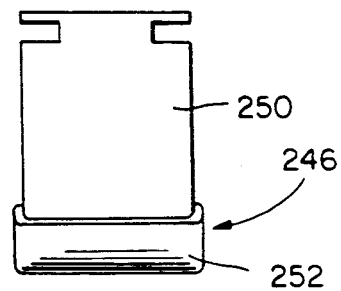
Figure 12:
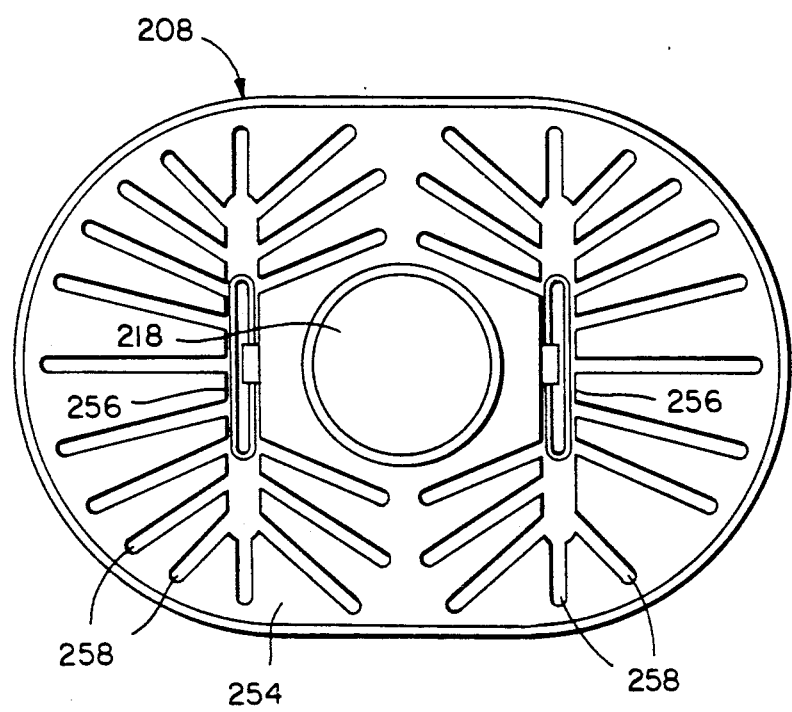
FIG. 12 is an underneath plan view of the pulsing electrode.

Each electrode assembly 208 additionally consists of a top plate 234 (see FIGS. 10a-10c), a housing cover 236, a compression plate 238, two U-shaped fluid container chambers 240, two conductive fluid-containing sacs or pouches 242, a compression spring 244, two puncture mechanisms 246, and a voltage controlled, heat operated release mechanism, to be described.

The chambers are permanently fastened to the housing cover with fold-over tabs 248. The compression plate 238 is installed beneath the housing cover 236, and between the compression plate and the bottoms of the chambers are situated the flexible sacs or pouches 242 containing the electrolyte or like conductive fluid.

Figure 13A:
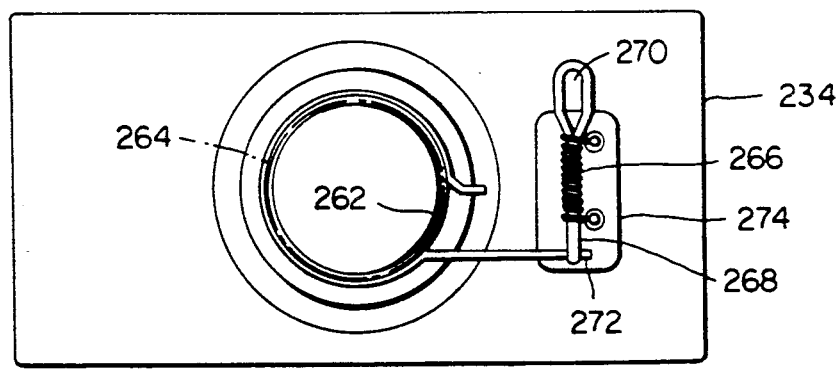
FIGS. 13a and 13b are respective plan views of a voltage controlled heat operated release mechanism, FIG. 13a being shown in the holding mode and FIG. 13b being shown in the operation mode.
Figure 13B:
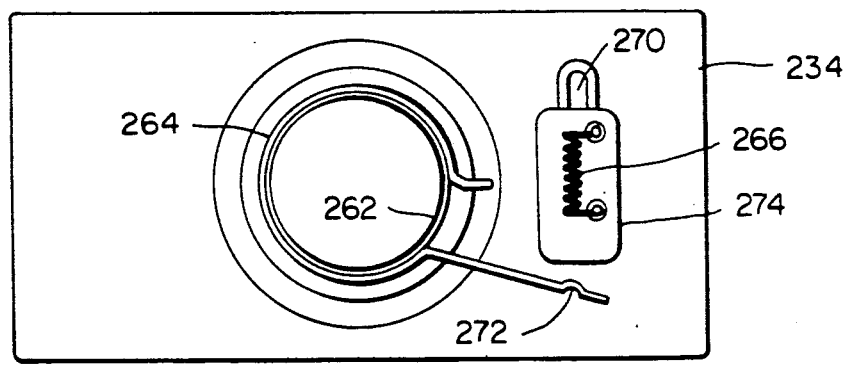

The plates 234 and 238 are held in close proximity by a heat operated release mechanism, consisting of a cylindrical release sleeve 262, a torsion spring 264 located in a peripheral groove 278 at the upper end of the release sleeve, a resistance wire heating element 266, and a synthetic fiber restraining member 268 (see FIGS. 13a, 13b). Member 268 is fastened at one end to a pierced tab 270, or like fastener formed in top plate 234, and at the other end to a deformed zone in the torsion spring 272. An insulating strip 274 is installed under the heating element to isolate it from the top plate and to provide a means to make electrical connections to the element.

A flange 276 on the lower end of the release sleeve engages the underside of the compression plate 238 and the groove 278 on the upper end of the sleeve engages the torsion spring 264. The spring, (when compressed), engages the upper side of the top plate.

Upon receipt of the appropriate signal from the pulse generator 210, upon detection of a treatable heart condition, the heating element 266 melts through the restraining member 268, releasing the free end of the torsion spring 264, which disengages from the groove in the release sleeve, freeing the top plate.

The compression spring 244, applies pressure against the top plate 234, causing it to move upward, (away from the skin), and carry with it the top half of the electrode housing 260, to which it is fastened. This movement, via the enclosed pockets 204 in the vest structure, and the reinforcements sewn within the vest, transmits radial pressure against the chest wall, reducing the impedance at the electrode/skin interface, and ensuring adequate pressure for effective pulse delivery.

Additionally, the compression spring 244 applies downward pressure upon the compression plate 238 and the release sleeve 262, which are free to move toward the skin. This downward pressure is transmitted to the fluid sacs 242. The puncture mechanisms include pointed members 250 attached to the compression plate, which move through respective retaining tubes 252 and puncture the bottom surfaces of the fluid containers, when places 234 and 238 are forced apart. As the compression plate moves through its travel, the fluid medium is forced out of the sacs into ports 256 and channels 254 situated in a bottom part of the electrode assembly, and by these means are transmitted to the pulsing electrode 258 and to the patient's skin surface, saturating this interface, and reducing the impedance thereby.

It will be apparent that electrode structures similar to structures 208 can also be employed in a harness-type garment which may include a belt, such as belt 14 and/or a shoulder strap, such as strap 18 as previously described.

In still another form of the invention, the impedance reducing mechanism may include a fluid-pressure actuated mechanism for increasing pressure of a pulse electrode against the patient's skin in response to a treatable heart condition being detected. Such fluid pressure actuated mechanism may include a gas cartridge for tightening an electrode-carrying belt or strap such as belt 14 or strap 18 previously described.

Figure 14:
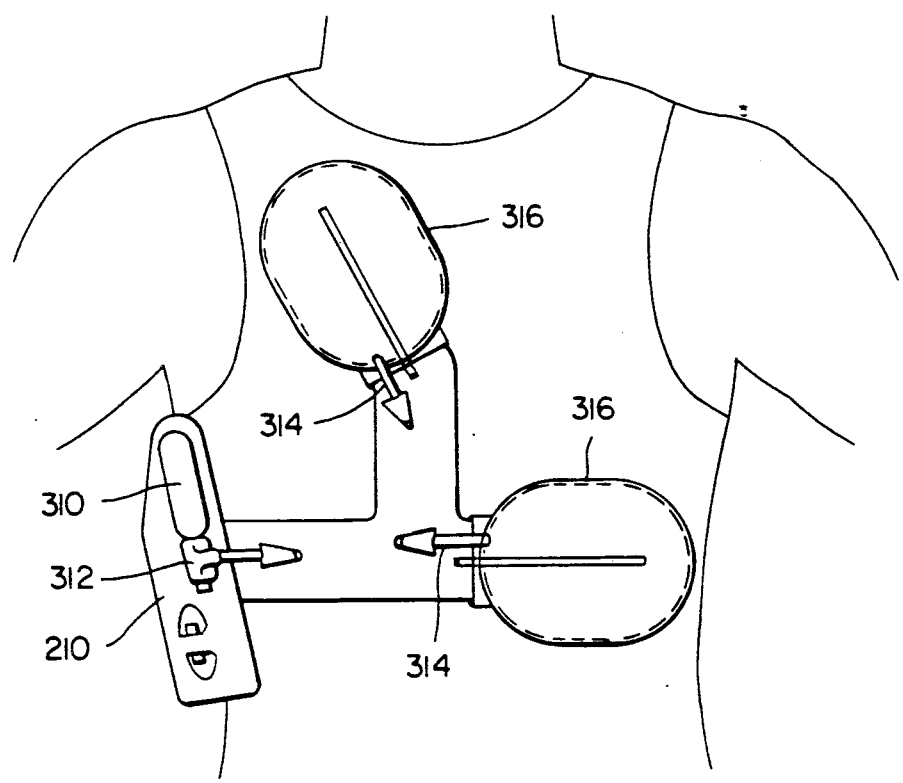
FIG. 14 is a diagrammatic in-use view of a third embodiment pacemaker/defibrillator as worn by a patient.

One such embodiment consists of a gas source, (pressurized cylinder) 310, FIG. 14, and an electrically-operated actuator, or squib, 312, located on or near the pulse generator package 210, with conduits 314, for carrying gas under pressure to each electrode housing 316, upon activation of the gas source.

Figure 16A:
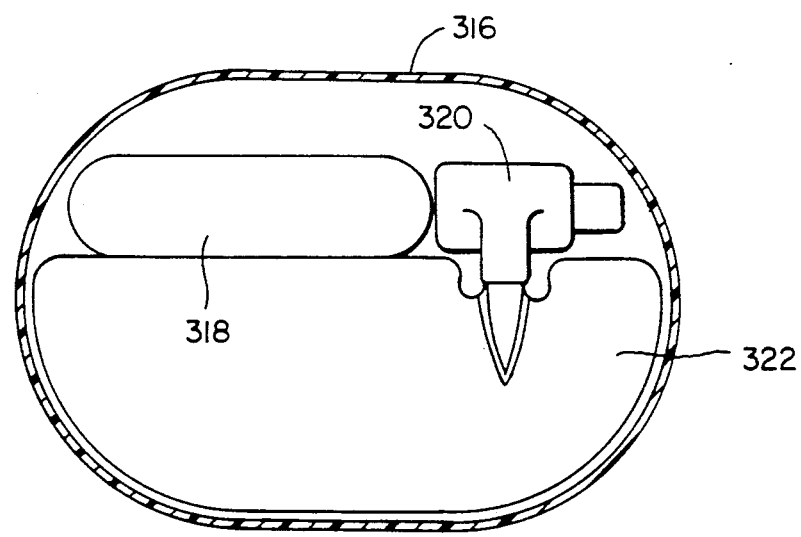
FIGS. 16a and 16b are respectively a plan view and an end view of the electrode housing with a gas source locally mounted within the pad housing.
Figure 16B:
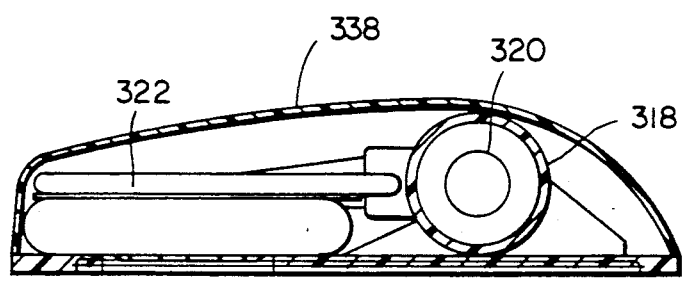
Figure 16C:
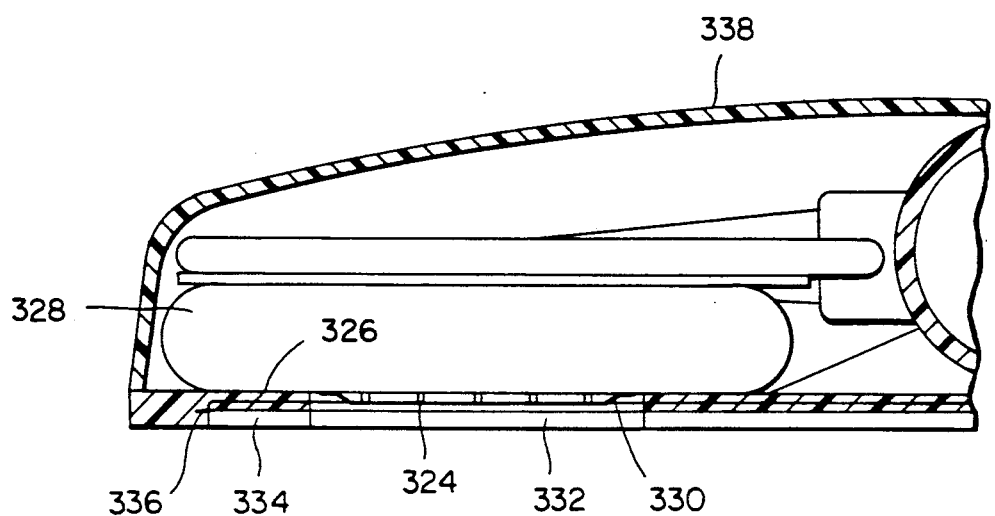
FIG. 16c is an enlarged end view showing increased detail of the electrode housing, including a fluid container, resistive heating element and retaining membrane.

A second such embodiment consists of a local gas source 318, and actuator 320, located in each electrode housing, as shown in FIGS. 16b and 16c.

Figures 15A, 15B:
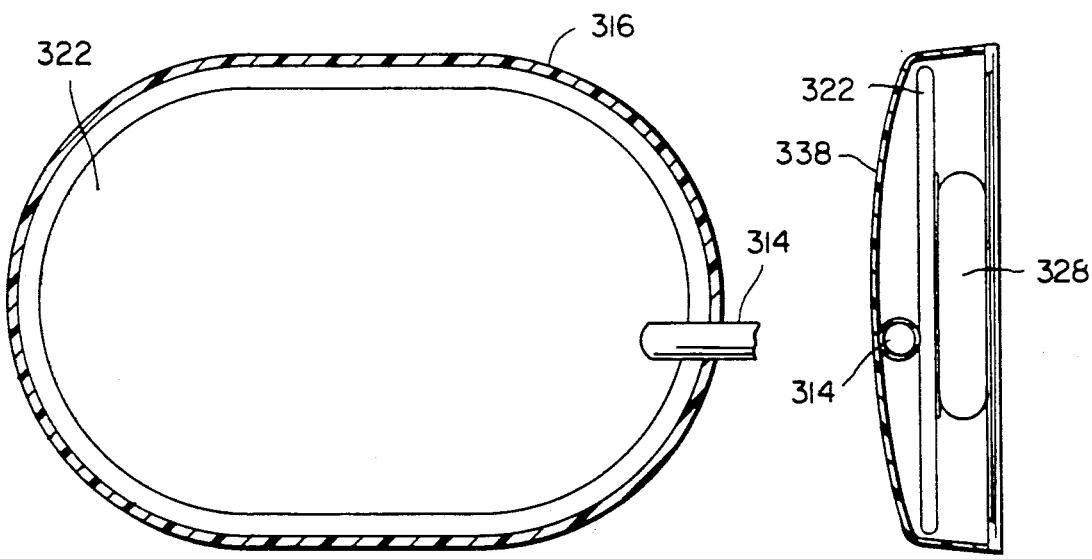
FIGS. 15a and 15b are respectively a plan view and an end view of an electrode housing with a gas source remotely mounted.
Figure 15C:
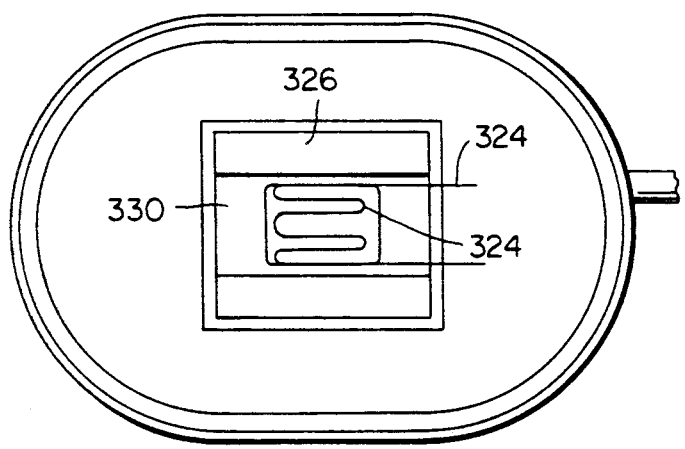
FIGS. 15c and 15d are respective bottom views of the electrode housing, with a fluid container, resistive heating element and retaining member being shown with channels being removed in FIG. 15c and being in place in FIG. 15d.
Figure 15D:
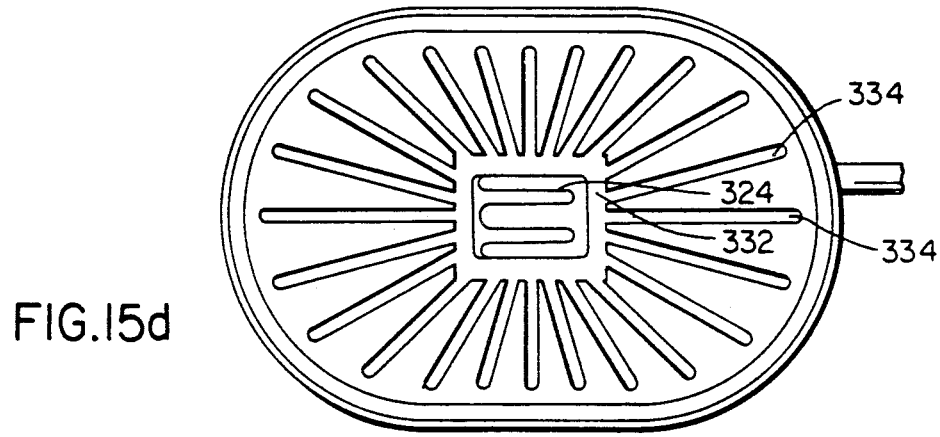

In both such embodiments, each electrode may have an inflatable cell or bladder 322, (FIGS. 15 and 16) which at activation expands, supplying movement in two directions.

At detection, an electrical signal is sent to the gas actuator, releasing the gas from the respective gas source and pressurizing the inflatable cell.

A resistive heater 234, held in proximity to the lower wall 326, of the fluid sac 328, by a thermally bonded membrane 330, or other attachment means, heats when activated, melting through the wall of the sac and the membrane, thereby releasing electrolyte fluid or gel from the sac.

Pressure supplied by the inflated cell squeezes the fluid out of the sac and into ports 332, and channels 334, as in the previous embodiments saturating the skin contacting treatment electrode 336, and the skin surface.

The movement of the cell by expansion is simultaneously transmitted to the upper housing half 338, of the electrode assembly causing it to move upward, away from the skin. This movement, via an enclosed pocket 204 in the vest structure, and the reinforcements sewn within the vest or garment, transmits radial pressure against the chest wall, reducing the impedance at the electrode/skin interface.

The monitoring base station may be equipped with a known volumetrically controlled source of gas that can check the integrity of the inflatable cell or bladder by verifying the maintenance of pressure subsequent to test gas inflation by the monitoring system.

The vest/harness structure is designed to provide sufficient slack space to permit long term wearing comfort. The structure is initially fitted prior to day-to-day wear to ensure that this slack space is restricted to a dimension less than the combined electrode expansion distances, ensuring adequate pressure for effective pulse delivery.

FIGS. 17-34 show electrical therapy treatment systems designed with the emphasis on patient comfort and to permit, to as great a degree as possible, concealment beneath everyday street clothing.

Figure 17:
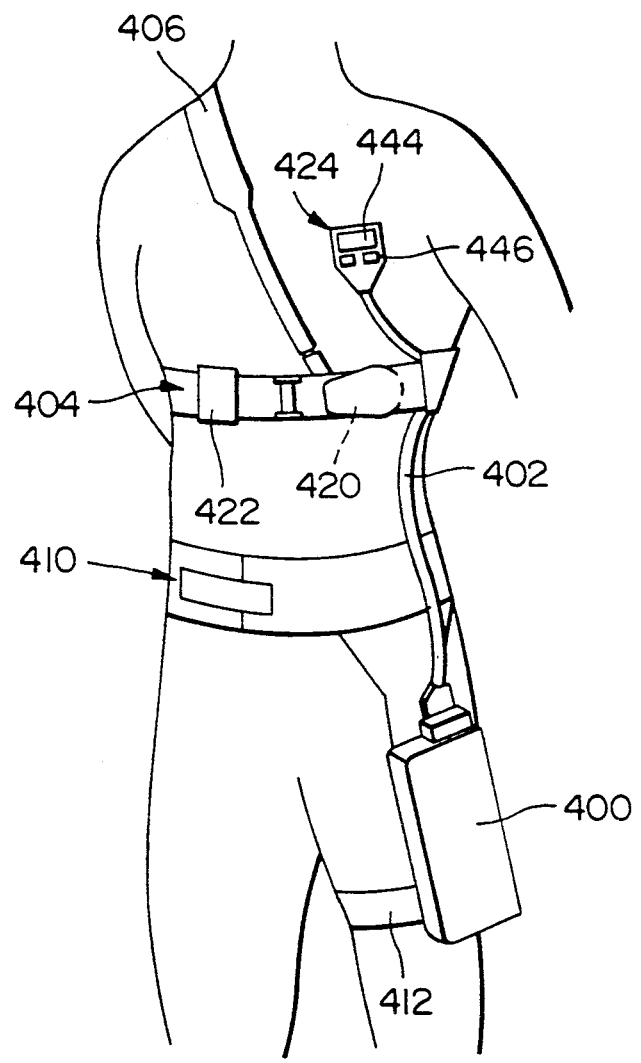
FIG. 17 is a partly diagrammatic in-use view of a third embodiment patient worn heart arrhythmia correction system with a chest belt and a treatment package worn on the upper left leg.

Referring to FIG. 17, a third embodiment of a patient-worn heart arrhythmia correction system consists of: an electronics package 400 (generally equivalent to pulse generator 24 of the previous embodiments), worn at the patient's upper left leg, and an interconnecting, flexible etched circuit conductor system, or optionally a flat cable 402, which extends between the electronics package and a circumferential belt and electrode assembly 404, worn around the upper chest.

An over the shoulder belt 406, containing an elasticized section 408 (FIG. 20,) imparting standby tension thereto, is connected to and supplies support to the circumferential belt 404.

A low waist or hip worn belt/holster combination 410, supplies support to the electronics package at the upper left leg position and may include a leg strap 412.

Figure 18A:
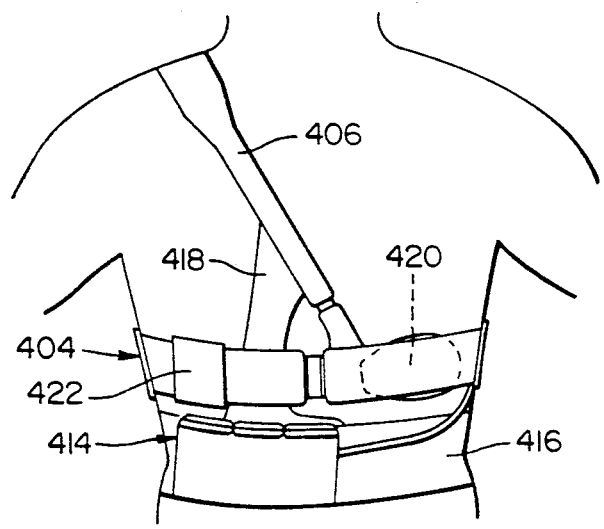
FIG. 18a is a partly diagrammatic in-use view of a fourth embodiment patient worn heart arrhythmia correction system with a chest belt and a treatment package worn on the lower right chest.

Referring to FIG. 18a, in a fourth embodiment, package 400 and hip belt 410 are replaced by an articulated or segmented electronics package 414, worn at the patient's lower right chest or at the waist and carried on a waist-worn belt 416, combined with a yoke 418, attached to the over shoulder belt 406, thereby supplying support to the electronics package at the chest position.

The chest belt 404 carries detecting or sensing electrode structures 422 for detecting a treatable condition in a patient along with treatment electrode structures 420 for applying electrical therapy upon detection of a treatable condition. These structures will be described in more detail hereinafter. The belt also carries a tethered read-out device 424.

The circumferential chest belt 404 in the forms illustrated in FIGS. 17 through 22 is largely constructed from various densities and thicknesses of polymeric closed cell foam. The structures may include metallic or non metallic spring members to impart selective loading or pressure upon the skin to maximize pressure to sensing and treatment electrodes carried by the belt and to minimize pressure to those zones performing no electrical function.

Figure 18B:
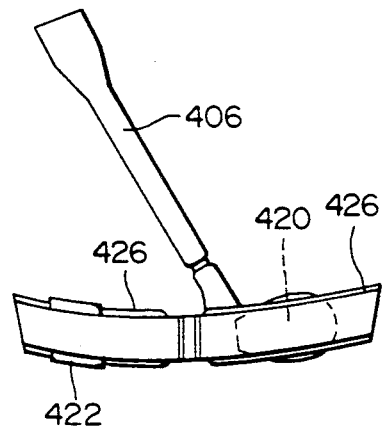
FIG. 18b is an in-use view of the front region of a chest belt of the type shown in FIGS. 17 and 18a with a full length circumferential elastic member in place.
Figure 18C:
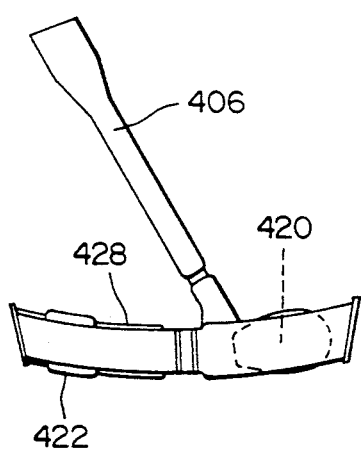
FIG. 18c is an in-use view of the front region of the chest belt with an elastic member applied to the patient's left front quadrant only.
Figure 18D:
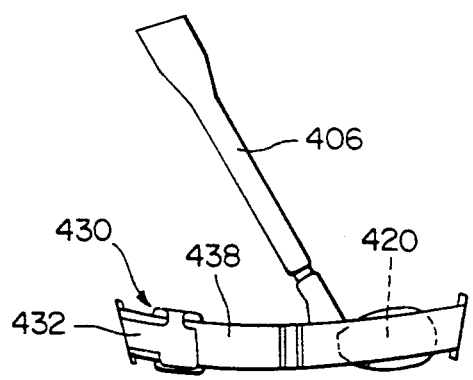
FIG. 18d is an in-use view of a further embodiment of the chest belt with a conductor system embedded within the outer perimeter of the belt and with sensing electrode structures integrated within a discontinuous inner perimeter of the belt, and with elastic tensioning means interposed between the perimeters.
Figure 18E:
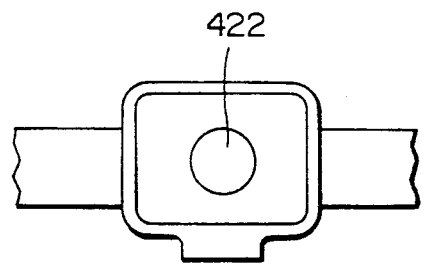
FIGS. 18e-18g are enlarged views of an electrode section of the belt structure shown in FIG. 18d.
Figure 18F:
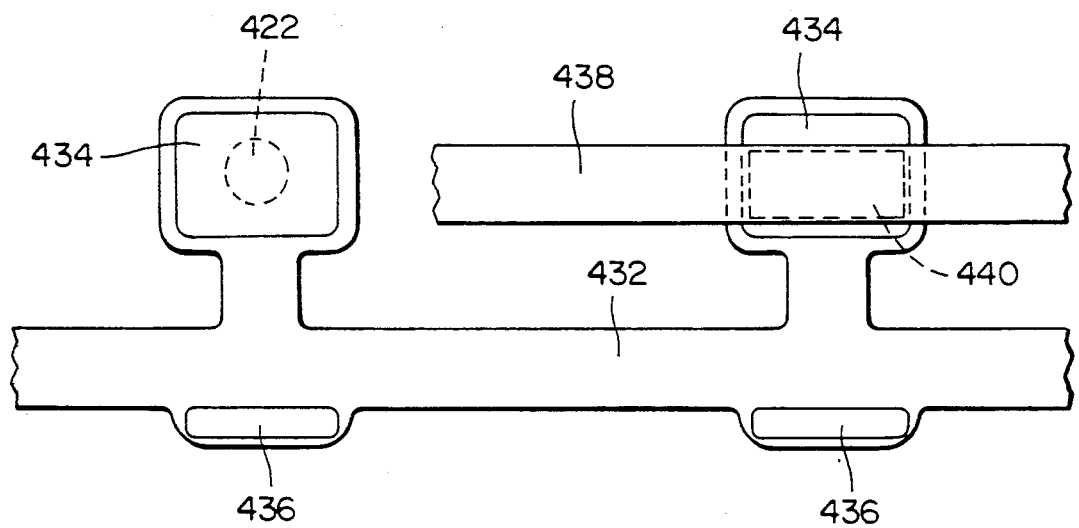
Figure 18G:
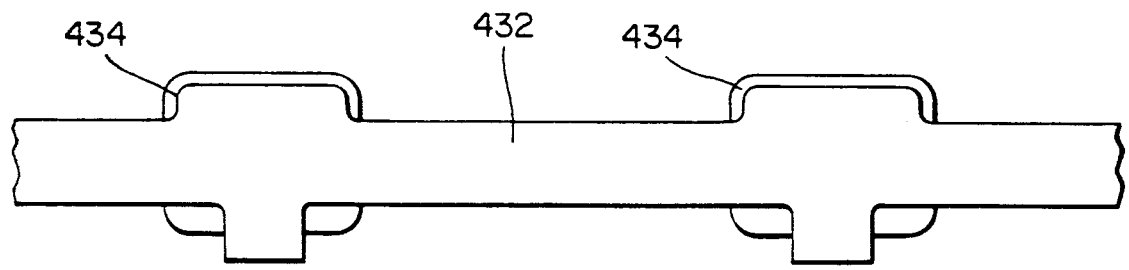

Referring to FIG. 18b, the chest belt has an elastic member or layer 426, applied over substantially the entire circumference of the chest belt. In FIG. 18c, the elastic member 428, is applied only to the patient's right front quadrant. In FIG. 18d, the belt has a laminated polymeric foam layer configured as a fold-over structure 430, with the sensing electrodes 422 contained therein and isolated from one another, forming the inner perimeter of the belt, and a conductor system 432 for the electrodes, embedded into a layer forming the outer perimeter of the belt. Hook 434, and loop 436 pile-type fasteners or other like means, are installed on the mating surfaces of the fold-over sections to impart consistent shape to the assembly. An elastic member 438 is applied between the inner and outer perimeters over the entire circumference of the belt and is attached to the sensing zones with further hook and loop pile-type fasteners 440 thereby imparting localized pressure to the zones and allowing for easy removal of the member for laundering.

Figure 19:
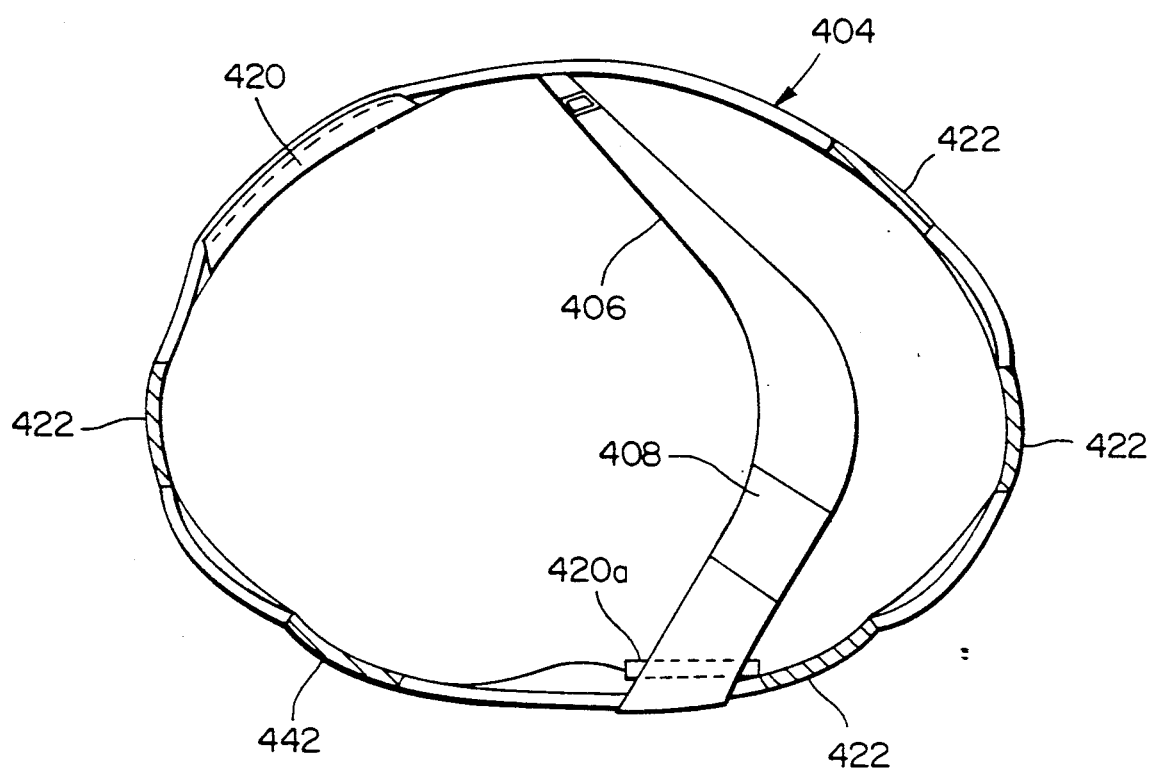
FIG. 19 is a plan view of the body-encompassing structures shown in FIGS. 17 and 18a, as seen from above the patient, with the upper chest belt shown in section.
Figure 20:
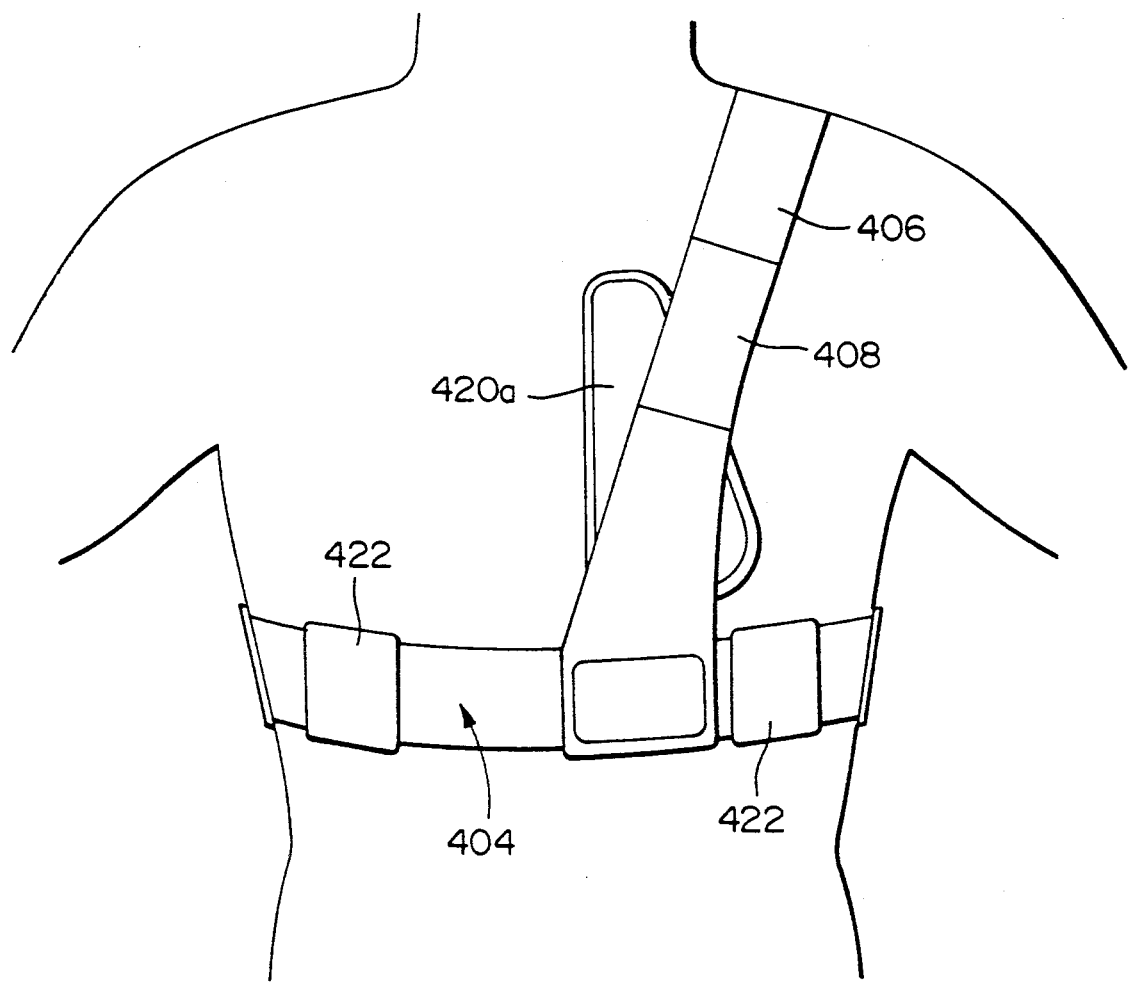
FIG. 20 is a partly diagrammatic in-use back view of the third and fourth embodiment chest belt/electrode structure.
Figure 21A:
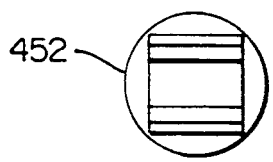
FIGS. 21a to 21c are underneath plan, side, and in-use views respectively of a belt adjustment locking device.
Figure 21B:
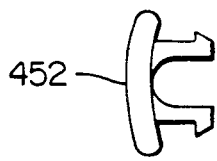
Figure 21C:
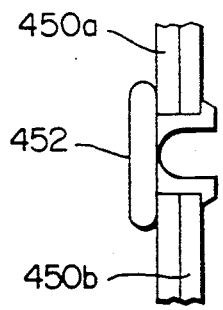
Figure 22A:
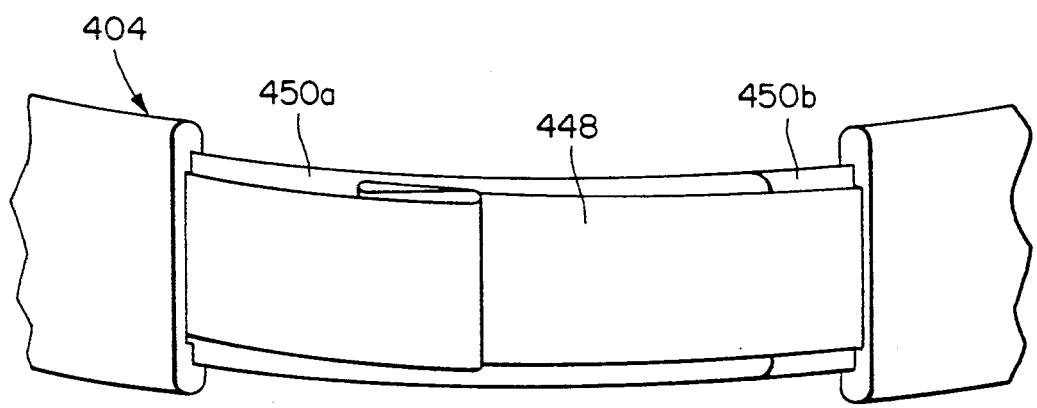
FIG. 22a is an enlarged detail view of an area of the belt near a rear treatment electrode and showing a belt adjustment means.
Figure 22B:
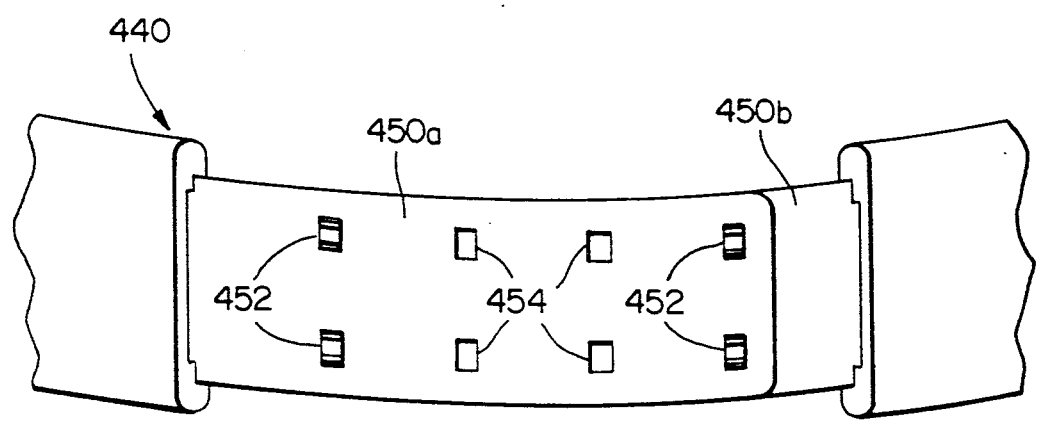
FIG. 22b is a view similar to FIG. 22a and showing a flexible conductor system folded over the adjustment means.
Figure 22C:
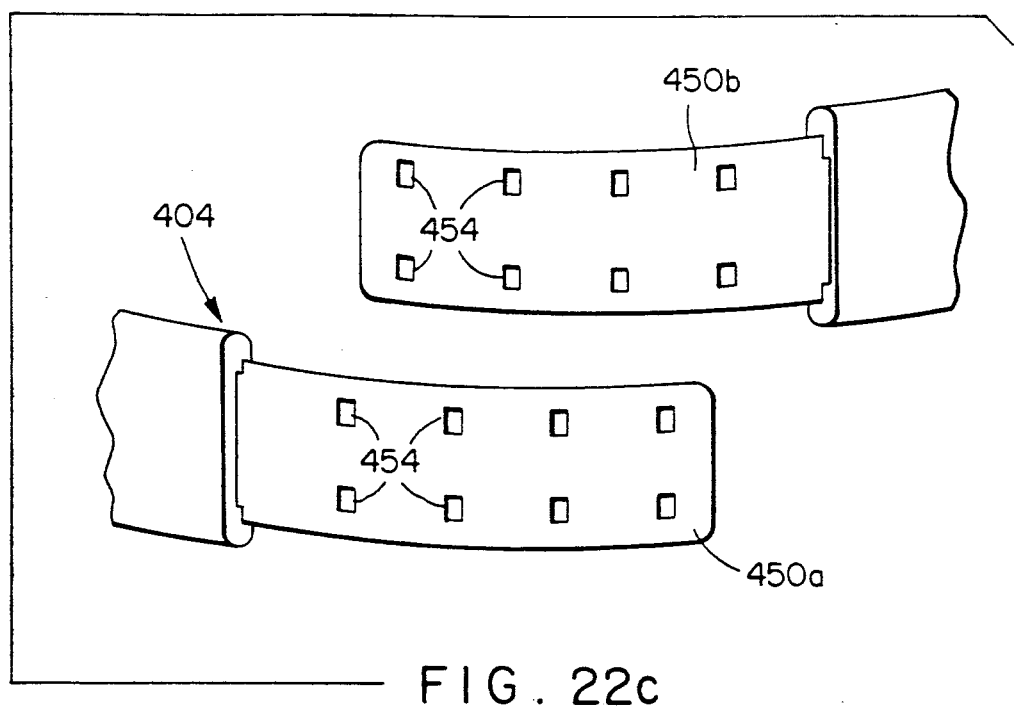
FIG. 22c is an opened out view of curved elastomeric members forming the adjustment means.
Figure 23A:
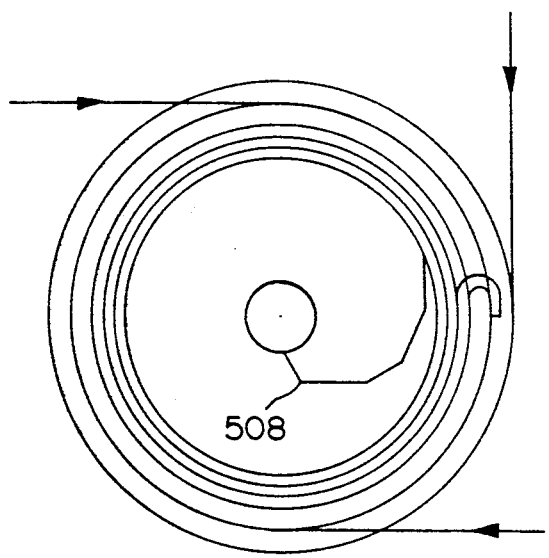
FIGS. 23a and 23b are front and side views of a power spring operated tensioning device.
Figure 23B:
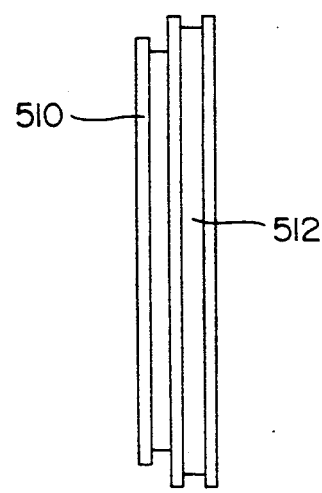
Figure 24:
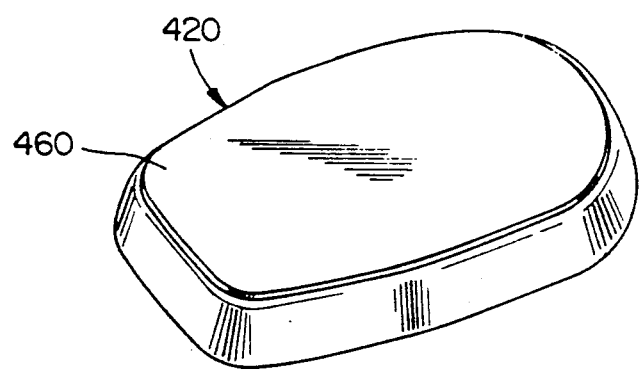
FIG. 24 is a perspective view of the front treatment electrode.
Figure 25:
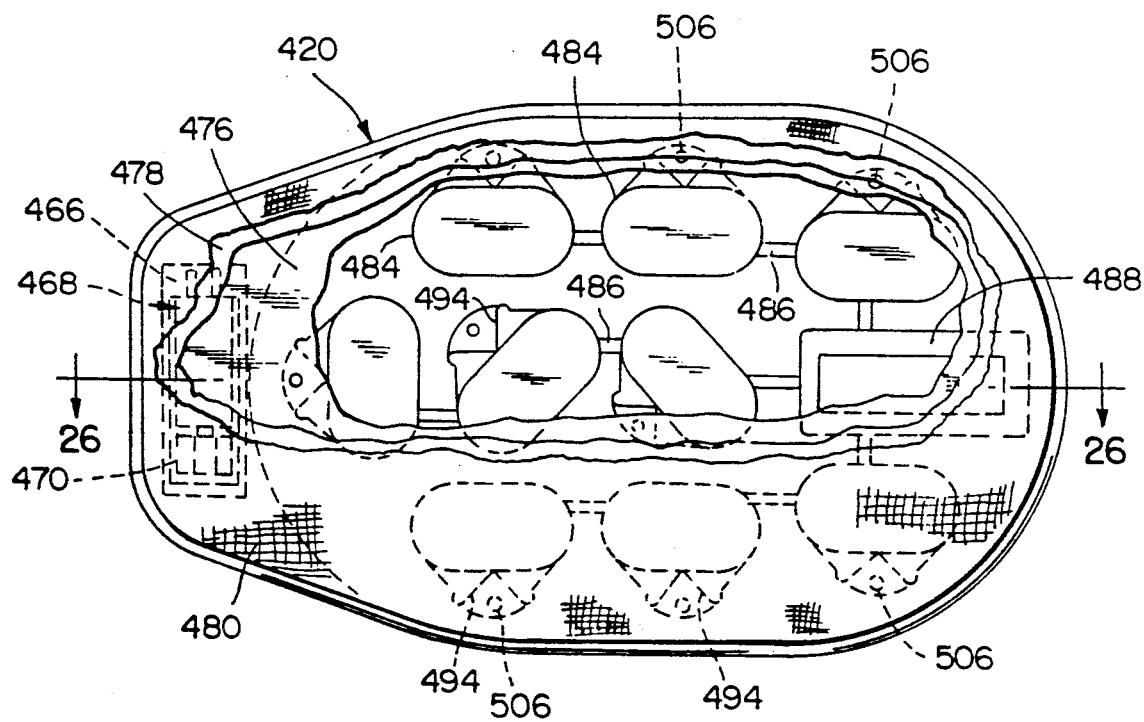
FIG. 25 is an underneath plan view of the front treatment electrode partly broken away.
Figure 29:
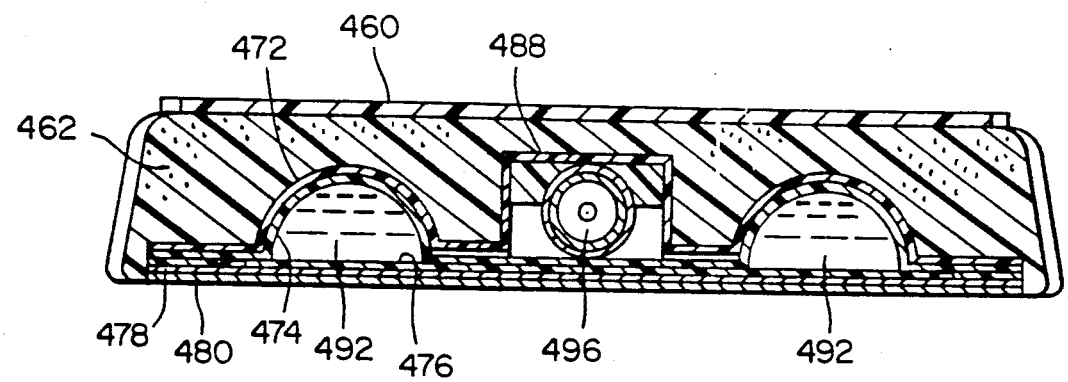
FIG. 29 is a sectional view on line 29—29 of FIG. 26.
Figure 30:
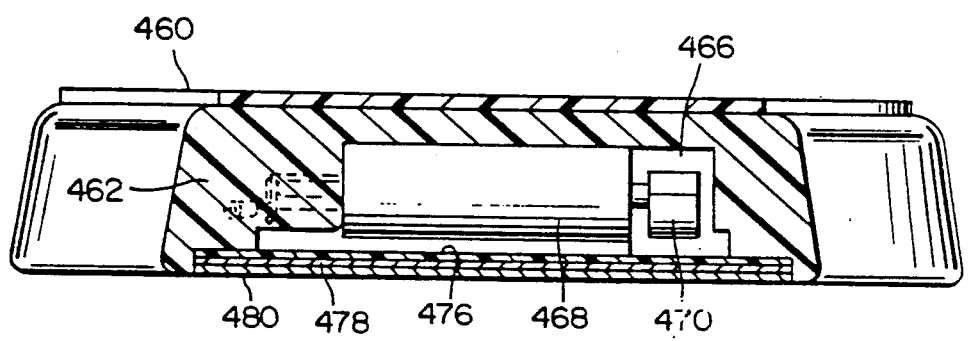
FIG. 30 is a sectional view on line 30—30 of FIG. 26.
Figure 31:
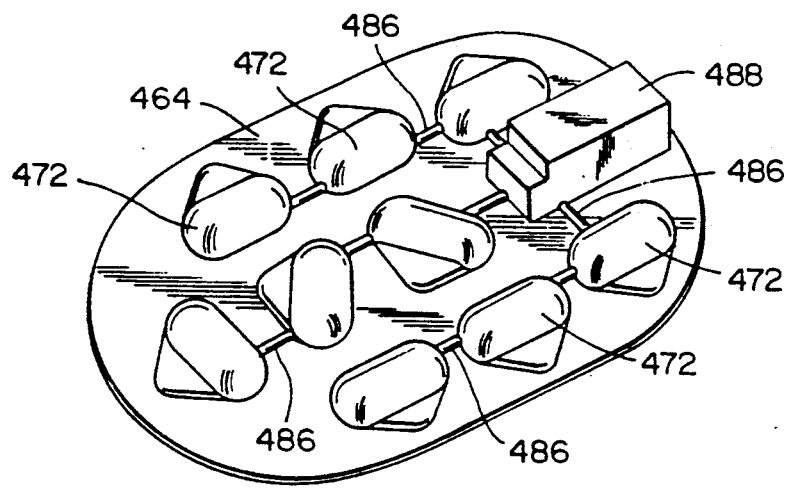
FIG. 31 is a perspective view of one layer of the front electrode structure.
Figure 35A:
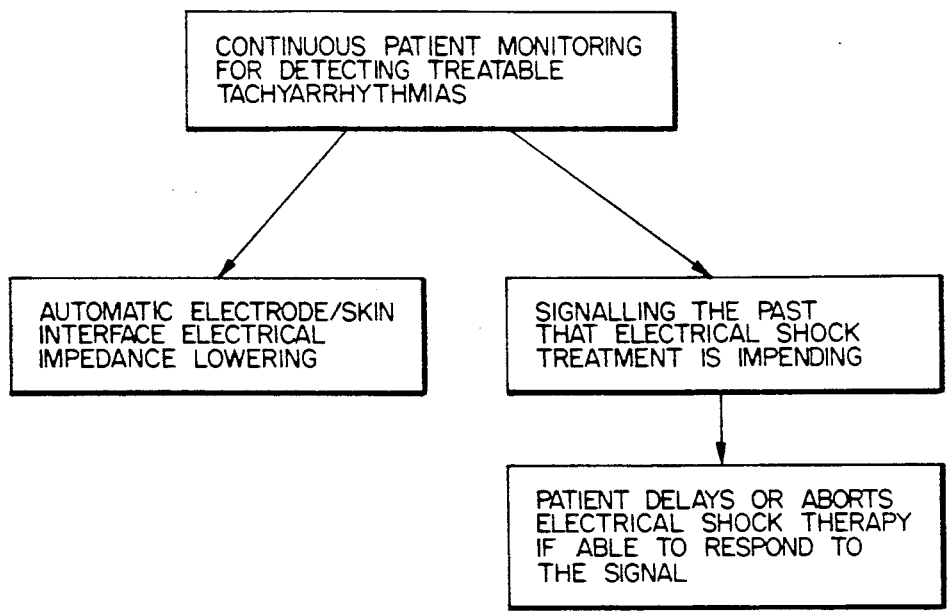
FIGS. 35a and 35b are block diagrams illustrating respective modes of operation of the afore-illustrated treatment apparatus.
Figure 35B:
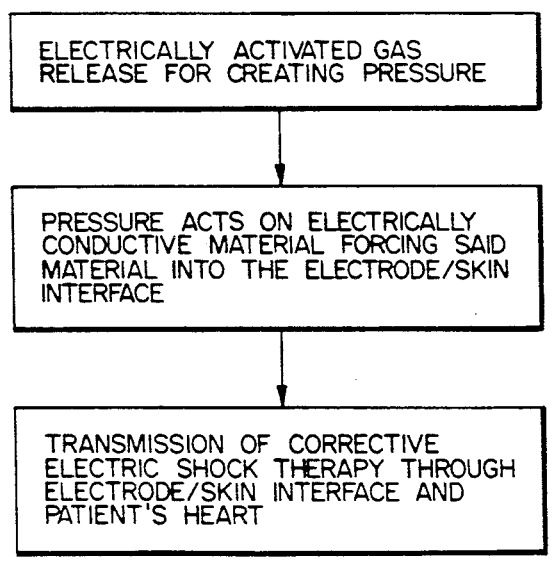

Referring to FIG. 19, integrated into the circumferential chest belt are the dry, electrocardiogram sensing electrodes 422, each with associated buffer amplifier, arranged in an orientation around the perimeter of the belt that permits two-axis ECG sensing, and a large-area reference electrode 442. Also integral to the chest belt is the readout means, 424 of FIG. 17, (not shown in FIG. 19) having a pocket clip, or like fastener on the housing, permitting visual messages to be sent to the patient by the electronics package computer, either via the tethering cable 402, or optionally via a radio link, to a display means 444 within the readout device. The device 424 may have means, such as an acknowledge switch 446, by which the patient may respond and acknowledge receipt of the message. The read-out device may have patient-operated switches for controlling the onset of therapy and allowing therapy to be initiated should the patient not respond to stimuli prompted by the apparatus, by operation of the switches (See FIG. 35a). With the tethered embodiment, the readout device and attached cable may be routed through the clothing from the chest belt, permitting attachment to a pocket or the like, thereby allowing unrestricted viewing and response by the patient. The untethered embodiment, utilizing the radio link, may be worn anywhere on the body that the patient may desire. Also integral to the chest belt are means to provide attachment for the interconnecting cable to the electronics package and electrical conductors such as the electrical conductors 432 of FIG. 18d and 18f. As shown in FIG. 22a, an electrical conductor 448 may be configured as a flexible etched circuit, or optionally as a flat cable, interconnecting the various electrodes on belt 404.

Also integral to the chest belt are shaped elastomeric members, 450a and 450b (FIGS. 22a-22c) curved to concentrate the circumferential forces imparted by the belt to the sensing electrodes and to space the belt sections between the electrodes away from the skin to enhance comfort during wear. Also integral to the chest belt are means to permit field adjustment of a given circumferential chest belt length to a range of patient chest sizes. Thus, the curved elastomeric members 450a and 450b, are noncontinuous across the patient's back, and are perforated in a pattern permitting coarse length adjustment by varying distances of overlap. Molded snap rivets 452 (FIGS. 21a-21c), or other like fastening means installed into the perforations 454 at fitting, provide a positive means of locking the members to the desired length that is not reversed easily. This ensures that the adjustment will impart the correct degree of tension to the circumferential belt and thereby the correct degree of pressure upon the sensing and treatment electrodes.

The treatment electrode 420 is approximately 11 cm × 6.4 in size and is electrically and mechanically attached to the circumferential chest belt, at the patient's left front. A like treatment electrode 420a, approximately 17 cm × 9 cm in size is electrically and mechanically attached to the chest belt and to the over the shoulder belt, at the patient's back, to the right of center and above the axis of the chest belt. These locations place the centers of area of the treatment electrodes on an axis lying through the heart. These electrodes, as in the previous embodiments, are designed to deliver therapeutic energy to the heart upon detection of a treatable arrhythmic event and to lower the electrode-to-skin impedance prior to delivery of the energy. The electronic aspects thereof are generally well known in the art and this invention is particularly concerned with the structural aspects of the electrodes and the impedance reducing means. The impedance reducing means consists, inter alia, of means for extruding a highly conductive fluid into the space between the treatment electrode surface and the patient's skin.

Referring to FIGS. 24 through 31, the front treatment electrode 420 (and the design of back treatment electrode is substantially the same) consists of a multi-layered laminate of various elastomeric materials. The outermost layer 460, (lying immediately beneath the under surface of the belt 404), is typically a polycarbonate or like plastic material, imparting strength and shape to the structure.

Next is a layer of closed-cell microporous elastomeric foam or like material 462, designed to impart softness to the assembly and which is formed, as shown in section, into cavities 464, affording protection to the inner layers of the electrode structure as will be described. An additional larger cavity 466, is molded into the foam layer of the front treatment electrode, to accept the housing of a tactile stimulator 468, integral to the belt structure. This device is a small electric motor with a shaft mounted off-center weight 470. The motor is designed to be energized for brief periods by a signal from the electronics package computer. The energizing of the motor vibrates the skin of the abdomen, and alerts the patient to respond to a message being displayed on the tethered readout device 424.

The inner layers of the treatment electrode comprise an outer conductive fluid containment layer 472, an inner fluid containment layer 474, a sealing layer 476, peelably welded to the surface of the inner fluid layer, and a highly-conductive treatment electrode layer 478. Interposed between the treatment electrode layer and the patient's skin is a soft, porous and changeable fabric material 480. Layers 472 and 474 are typically elastomeric thin films, having low rates of water vapor transmission, thermoformed into blisters 482 each approximating a half cylinder in shape. Dimensional differences between the formed blisters permit the blisters of layer 474 to be intimately nested within the blisters of layer 472. Welds 484 are made around the perimeters of the nested blisters, except for zones 486, which comprise shallow, thermoformed channels interconnecting all the blister sets within a treatment electrode. These channels eventually connect to a larger thermoformed blister set 488, containing an electrically operated gas generating source 490.

At manufacture, the blisters formed in the inner containment layer 474 are filled with a conductive fluid 492, and the sealing layer 476, is then welded into place, using a Vee-shaped weld geometry at each blister as indicated at 494.

The internal components of the gas generating source are a gas-generating cartridge 496, intimately fitted within a thermally-conductive pressure chamber 502, and a porous plug of high temperature filtration media 498, intimately fitted within the opposite end of the pressure chamber. This end of the chamber is also fitted with a small diameter orifice 500. The structure described is perimeter welded into the larger blister 488.

Upon detection of a treatable arrhythmic event, an electrical signal is sent to the gas generating cartridge, igniting a chemical pellet within, composed of a Lead Styphnate igniter and a gas generating mixture of Ammonium Dichromate and Nitroguanidine which rapidly decomposes, generating quantities of Nitrogen gas. The gas is vented into the pressure chamber 502 through a rupturable membrane 504, in the end of the generator housing. The gas is then cooled by conduction to the walls of the pressure chamber, passes through the filtration media 498, and the orifice 500, where it is filtered, restricted and cooled further, and is then vented into the larger blister set 488.

From the larger blister, the gas is forced by expansion into the gas channels 486, weld-formed into the electrode laminate, pressurizing the volume between each two nested, thermoformed blisters 472 and 474.

As pressure increases, the mating, but unwelded surfaces of the blisters 472 and 474 are forced apart and the inner blisters 474 invert into the conductive fluid. The resultant force on the fluid applies hydraulic pressure to the seal layer film 476, on the underside of the assembly, delaminating the fracturable Vee welds 494 (see FIG. 28), and forcing the fluid to extrude through ports 506 in layer 476, onto the skin contacting treatment electrode layer 478 and into the small space between this layer and the skin surface. To this end, layer 478 may be porous or may be formed with suitable fluid openings.

The fluid wets the interface, including the interposed fabric, and thereby reduces the impedance thereof.

In addition to the conductive fluid impedance reducing means, further reduction means may include a spring powered means for increasing the pressure of the treatment electrodes against the patient's skin in response to a treatable heart condition being detected. A power spring 508, (FIG. 23a), released by an electrical signal from the electronics package simultaneously with the signal that activates the gas generators, applies rotational force to two differing diameter drums 510 and 512. Metallic or non-metallic tension members as described within relation to the previous embodiments, are wound around the drum circumferences and are threaded through channels molded or formed into the outer covering of the chest belt structure. The members, as tensioned by the power spring at activation, impart 0.5 to 6 pounds additional tensile force on each of the belts, circumferential and over the shoulder. These increases in tension upon the belts enhance the electrode to skin pressure significantly thereby further reducing the impedance.

Figure 32A:
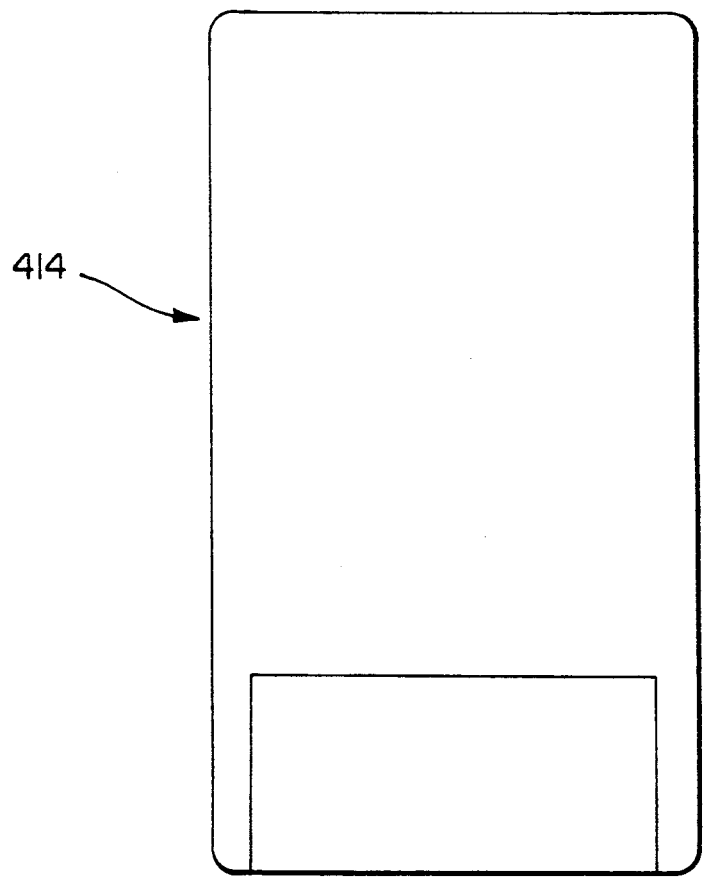
FIGS. 32a and 32b show an end view and a plan view of a leg worn treatment package.
Figure 32B:
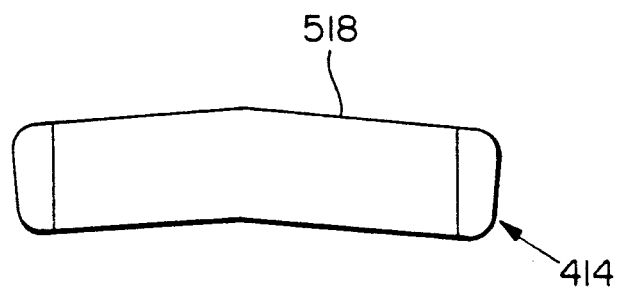

FIGS. 33a-33c show one embodiment of the segmented chest worn treatment package 414. The electronics are divided into three segments 414b and 414c cased within molded shells 514a, 514b and 514c. The case shells are radiused at 516 to fit intimately to the body curvature, ensuring comfortable long term wear. Additionally, the case shells may be molded into compound curves, in the vertical and lateral planes, conforming respectively to either the curvature of the upper leg, as shown in FIG. 32b at 518, or to the curvature of the chest, as shown in FIG. 18.

Conventional printed wiring boards 520, are utilized in this embodiment, with the interconnection between segments consisting of conventional ribbon wire conductors 522. A flexible elastomeric gasket 524 provides environmental sealing to the conductors and the interfaces of the segments.

Alternately, as shown in FIGS. 34a and 34b, the electronics system may be fabricated using a "rigid-flex" construction wherein a flexible printed conductor wiring substrate 526, is laminated to various zones of rigid printed circuit board 528, containing the active components of the device.

While only preferred embodiments of the invention have been described herein and in detail, the invention is not limited thereby and modifications can be made within the scope of the attached claims.

What is claimed is:

1. An electrode assembly for delivering electrical therapy to the body of a patient responsive to sensing of the occurrence of a treatable condition, comprising:
    electrode means having a conductive surface adapted for placement adjacent the patient's skin, for applying appropriate electrical pulses to the patient; and
    impedance reducing means, contained within said electrode means for delivery to the patient's skin by said electrode means responsive to sensing of said treatable condition by a sensing means, for reducing the impedance between the conductive surface of the electrode means and the patient's skin.

2. The assembly as claimed in claim 1, wherein said impedance reducing means comprises means for releasing conductive fluid between the conductive surface of said electrode means and the patient's skin.

3. The assembly as claimed in claim 2, wherein said means for releasing conductive fluid is contained in a housing and comprises:
    a fluid container chamber;
    a fluid containing sac located within said fluid container chamber; and
    a puncture mechanism for puncturing said fluid containing sac.

4. The assembly as claimed in claim 2, further comprising channel means in the conductive surface of said electrode means for receiving the conductive fluid and spreading the same over the conductive surface.

5. The assembly as claimed in claim 2 wherein the fluid is contained in at least one flexible fluid sac within the assembly, and wherein the means for releasing includes pressure means for squeezing the sac, and means for establishing a connection between the sac and said conductive surface responsive to operation of the pressure means for delivering fluid under pressure from the sac to said conductive surface.

6. The assembly as claimed in claim 5 wherein the means for establishing a connection comprises sealed conduit means extending between said sac and said surface, said conduit means being adapted to be forced open by pressure exerted thereon from the fluid in the sac responsive to operation of the pressure means.

7. The assembly as claimed in claim 5 wherein the conduit means is comprised of two laminated layers of sheet material which also comprise the sac.

8. The assembly as claimed in claim 7 which includes a third layer of sheet material laminated over one of said two layers and forming therewith a gas pressure chamber over the sac, the pressure means including means for supplying gas under pressure to said chamber for squeezing the sac.

9. The assembly as claimed in claim 5 future comprises a gas pressure chamber means over a least a part of an external surface of the sac, and the pressure means includes means for supplying gas under pressure to said chamber for squeezing the sac.

10. The assembly as claimed in claim 9 wherein the sac is comprised of two laminated layers of sheet material and wherein the pressure chamber is defined between one of said layers and a third layer of sheet material which is laminated thereto.

11. The assembly as defined in claim 10 wherein the means for establishing a connection comprises sealed conduit means comprised of the two laminated layers and adapted to be forced opened by pressure fluid from the sac responsive to operation of the pressure means.

12. The assembly as defined in claim 11 wherein the sac, the pressure chamber and the conduit means are replicated over an area of said laminated layers, and wherein channels are comprised of said one of said laminated layers and said third laminated layer for connecting the respective chambers to a common source of pressurized gas.

13. The assembly as claimed in claim 5 wherein the pressure means comprises a chamber means around at least a part of the sac for receiving gas under pressure for squeezing the sac, a source of pressurized gas and transfer means for the gas between said source and said chamber.

14. The assembly as claimed in claim 13 wherein the source of gas under pressure comprises a cartridge within the assembly containing an electrically activated gas-generating chemical.

15. An electrode assembly for automatically delivering electrical therapy to the heart of a patient upon the occurrence of a treatable heart arrhythmia, comprising:
electrode means adapted for contact with a patient's skin, for sensing the existence of a treatable arrhythmia and applying appropriate electrical pulses to the heart; and
impedance reducing means, contained with said electrode means and delivered to a patient's skin by said electrode means responsive to sensing of said arrhythmia by a sensing means, for reducing the impedance between the electrode means and the patient's skin.

16. The assembly as claimed in claim 15, further comprising:
monitoring means for continuously monitoring a patient's heart condition from the information sensed by said electrode means;
discrimination means for receiving signals from said monitoring means and determining the presence of a treatable heart arrhythmia from stored information;
a source of electrical energy; and
switching means actuated by said discrimination means in response to said determination of a treatable arrhythmia for connecting said source of electrical energy to said electrode means for applying appropriate electrical pulses to the heart.

17. The assembly as claimed in claim 16, further comprising channel means in the conductive surface of said electrode means for receiving the conductive fluid and spreading the same over the conductive surface.

18. The assembly as claimed in claim 15, wherein said conductive fluid is contained in a housing comprising:
a fluid container chamber;
a fluid containing sac located within said fluid container chamber; and
a puncture mechanism to puncture said fluid containing sac for releasing conductive fluid.

19. An electrode assembly for applying electrical therapy to the heart of a patient, comprising:
monitoring means for continuously sensing a patient's heart condition;
discrimination means for receiving signals from said monitoring means and determining the presence of a treatable heart arrythmia;
conductive electrode means adapted to contact the patient's skin;
a source of electrical energy;
switching means actuated by said discrimination means in response to determination of a treatable arrhythmia for connecting said source of electrical energy to said conductive electrode means for applying appropriate electrical pulses to the heart; and
impedance reducing means for releasing a conductive fluid between said conductive electrode means and the patient's skin to reduce impedance therebetween and responsive to said discrimination mean upon detection of said treatable heart arrhythmia by a sensing means.

20. The assembly as claimed in claim 19, further comprising signal generating means actuated by the discrimination means responsive to detection of a treatable arrythmia for warning the patient of the impending application of an electrical pulse, and a patient-activated switch means for delaying the connection of the source of electrical energy to the conductive electrode means.

21. The assembly as claimed in claim 20, wherein said switching means comprises two switches, both of which must be activated to delay connection of the source of electrical energy to the conductive electrode means.

22. The assembly as claimed in claim 19, further comprising channel means in a surface of said conductive electrode means for receiving fluid and spreading the fluid over the surface.

23. An electrode assembly for delivering electrical therapy to the body of a patient upon the occurrence of a treatable condition comprising:
a layer of conductive material for placement adjacent a patient's skin for applying appropriate electrical pulses to the patient;
a first sheet of flexible material positioned over the conductive material;
a second sheet of flexible material laminated over the first sheet, and forming in combination therewith;

(a) a least one fluid-containing at least one sac (b) conduit means for connecting said at least one sac with said layer of conductive material; and (c) a frangible seal between the at least one sac and the conduit means;

a third sheet of flexible material laminated over the second sheet and defining therewith at least one chamber at least partly surrounding said at least one sac for receipt therein of gas under pressure effective for squeezing said at least one sac so as to pressurize the fluid therein thereby fracturing said seal and allowing fluid from the at least one sac to pass through said conduit means to the layer of conductive material for reducing impedance between said layer and the patients skin; and gas supply means for supplying gas under pressure to said at least one chamber upon detection of said treatable condition.

24. An assembly as claimed in claim 23 wherein the at least one sac, the conduit means, the frangible seal and the at least one chamber are replicated over a common area of said sheets and wherein the gas supply means is connected to each of the respective chambers.

25. An assembly as claimed in claim 24 which includes passage means connecting at least two of said chambers defined between the second and third sheets for the delivery of gas between the chambers.

26. An assembly as claimed in claim 23 wherein the second and third sheets have respective nesting blister formations, forming said at least one chamber therebetween, and the blister formation in the second sheet forming said fluid-containing sac in combination with an area of the first sheet.

27. An assembly as defined in claim 23 wherein the gas supply means comprises a compartment in the assembly containing an electrically activated gas generating chemical substance and passage means comprised of said second and third sheet for connecting said compartment to said chamber.

28. As assembly as defined in claim 23 which includes a compartment containing a tactile stimulator for applying mechanical stimulation to the patient's skin responsive to a signal received by the stimulator.

29. An assembly as defined in claim 28 wherein the stimulator comprises an electric motor with a shaft-mounted off-balance weight.

30. A system for applying electrical therapy to a patient upon detection of a treatable condition comprising detection electrode means for contacting the patient's skin to detect the treatable condition, treatment electrode means for contacting the patient's skin for applying electrical impulses thereto responsive to the detection of the treatable condition, electronic means including a source of electrical energy for supplying electrical pulses to the treatment electrode means and discrimination means for receiving electrical impulses from the detection electrode means and actuating said source of electrical energy, readout means connected with the electronic means to provide a visible readout including the treatable condition, and tactile stimulation means connected to the source of electrical energy for applying mechanical stimulation to the patients skin prompting the patient to view the readout means.

31. A system as defined in claim 30 wherein the detection electrode means, the treatment electrode means, the tactile stimulation means and the electronic means are all carried by a body-encompassing structure and the readout means extends from said structure on a flexible lead.

32. A system as defined in claim 31 wherein the bodyencompassing structure includes a first chest-encompassing belt carrying the detection electrode means, the treatment electrode means and the tactile stimulation means, and wherein said lead extends from said chest-encompassing belt.

33. A system as defined in claim 32 wherein said body encompassing structure includes a waist-encompassing belt and said electronic means is suspended from said waist encompassing belt.

34. A system as defined in claim 32 wherein said body encompassing structure includes a second chest-encompassing belt below the first chest-encompassing belt, and the electronic means is carried by the second chest-encompassing belt.

35. A system for applying electrical therapy to a patient upon detection of a treatable condition comprising a first body-encompassing structure having a first belt for surrounding the patient's chest and an over-the shoulder strap connected to the first belt, a second body-encompassing structure including a second belt for surrounding the patient's torso below the first belt, detection electrode means carried by said first structure for contacting the patient's skin and detecting a treatable condition, treatment electrode means carried by the first structure for contacting the patient's skin and applying electrical therapy to the patient upon the detection of the treatable condition, electronic means supported by the second structure for receiving signals from the detection electrode means and delivering electrical pulses to the treatment electrode means, and electrical conductor means connecting the electronic means to the electrode means and to the treatment electrode means.

36. A system as claimed in claim 35 wherein the second belt has a suspended holster structure for supporting the electronic means against the patient's upper leg region.

37. A system as claimed in claim 35 wherein the second belt is adapted to surround the patient's chest below the first belt and has a support for the electronic means on the second belt.

38. A system as claimed in claim 37 wherein the second belt and the over-the-shoulder strap are interconnected by a yoke.

39. A system as claimed in claim 37 wherein the electronic means includes a flexible housing means adaptable to the curvature of the patient's chest.

40. A system as claimed in claim 39 wherein the housing means includes a plurality of separate housing elements each containing parts of the electronic means with mechanical and electrical connections between said housing elements and said parts respectively.

41. A system as claimed in claim 35 which includes a remote read-out device connected by an elongate flexible lead to said electronic means.

42. A system as claimed in claim 35 wherein the treatment electrode means comprises a first treatment electrode positioned on the first body-encompassing structure for location over the patient's heart, and a second treatment electrode positioned on the first body-encompassing structure for location against the patient's back.

43. A system as defined in claim 42 wherein the second treatment electrode has a larger skin-contacting area than the first treatment electrode.

44. A system as defined in claim 42 wherein each treatment electrode comprises impedance reducing means for reducing impedance between the electrode and the patient's skin upon detection of the treatable condition.

45. A system as claimed in claim 44 wherein the impedance reducing means comprises means for extruding an impedance-reducing fluid from the electrode to flow between a treatment surface of the electrode and the patient's skin.

46. A system as claimed in claim 45 wherein the impedance reducing means comprises at least one squeezable fluid sac within the electrode a sealed conduit between the sac and the treatment surface of the electrode, a frangible seal between the sac and the conduit, and pressure means for squeezing the sac upon detection of the treatable condition applying pressure to the fluid contained therein effective for breaking said seal and allowing the fluid to flow to said treatment surface.

47. A system as claimed in claim 46 wherein the pressure means includes a pressure chamber around a part of the sac for receiving gas under pressure effective for squeezing the sac, a source of gas under pressure contained within the electrode and means for delivering gas under pressure from the source to the chamber upon detection of the treatable condition.

48. A system as claimed in claim 47 wherein the source of gas under pressure includes an electrically activated gas producing chemical substance contained in a compartment within the electrode said compartment being connected to said pressure chamber by at least one gas passage.

49. A system as claimed in claim 35 wherein the detection electrode means comprises plural detection electrodes positioned on said first body-encompassing structure for multi-axis sensing of a treatable condition.

50. A system as claimed in claim 35 wherein the first belt comprises an endless first layer which includes conductor means for the electrode means and a second layer with opposite end portions and attachment means for releasably connecting the end portions in a plurality of selected positions adjusting the overall length of the second layer.

51. A system as claimed in claim 50 wherein the end portions of the second layer are substantially non-extensible and the second layer includes an elastically extensible portion between said end portions.

52. A system as claimed in claim 35 wherein the first belt includes tightness increasing means for increasing the tightness of the belt and thereby reducing impedance between the treatment electrode means and the patient's skin upon detection of the treatable condition.

* * * * *